United States Patent
Miasnikov

(10) Patent No.: US 10,450,575 B2
(45) Date of Patent: Oct. 22, 2019

(54) INCREASING THE EXPRESSION OF A TRANSGENE IN EUKARYOTIC CELLS BY REDUCING RNA INTERFERENCE

(71) Applicant: DANISCO US INC., Palo Alto, CA (US)

(72) Inventor: Andrei Miasnikov, Union City, CA (US)

(73) Assignee: DANISCO US INCCA (US)

( * ) Notice: Subject to any disclaimer, the term of this patent is extended or adjusted under 35 U.S.C. 154(b) by 0 days.

(21) Appl. No.: 14/909,927

(22) PCT Filed: Jul. 31, 2014

(86) PCT No.: PCT/US2014/049159
§ 371 (c)(1),
(2) Date: Feb. 3, 2016

(87) PCT Pub. No.: WO2015/020876
PCT Pub. Date: Feb. 12, 2015

(65) Prior Publication Data
US 2016/0177319 A1    Jun. 23, 2016

Related U.S. Application Data

(60) Provisional application No. 61/863,829, filed on Aug. 8, 2013.

(51) Int. Cl.
| | | |
|---|---|---|
| *C12N 9/22* | (2006.01) |
| *C12N 15/67* | (2006.01) |
| *C12N 15/63* | (2006.01) |
| *C12N 15/85* | (2006.01) |
| *C12N 9/12* | (2006.01) |
| *C12N 9/16* | (2006.01) |
| *C12N 9/30* | (2006.01) |
| *C12N 9/42* | (2006.01) |
| *C12N 9/48* | (2006.01) |
| *C12N 15/80* | (2006.01) |

(52) U.S. Cl.
CPC .............. *C12N 15/67* (2013.01); *C12N 9/127* (2013.01); *C12N 9/16* (2013.01); *C12N 9/242* (2013.01); *C12N 9/2437* (2013.01); *C12N 9/485* (2013.01); *C12N 15/63* (2013.01); *C12N 15/80* (2013.01); *C12N 15/85* (2013.01); *C12Y 207/07048* (2013.01); *C12Y 301/26003* (2013.01); *C12Y 302/01001* (2013.01); *C12Y 302/01091* (2013.01); *C12Y 304/14* (2013.01)

(58) Field of Classification Search
CPC ....... C12N 2310/14; C12N 15/67; C12N 9/16
See application file for complete search history.

(56) References Cited

U.S. PATENT DOCUMENTS

| | | | | |
|---|---|---|---|---|
| 7,282,564 B2 * | 10/2007 | Mello | .............. | C07K 14/43545 435/252.3 |
| 2012/0107872 A1 | 5/2012 | Ward | | |

FOREIGN PATENT DOCUMENTS

| | | |
|---|---|---|
| WO | 2000/032785 A1 | 6/2000 |
| WO | 00/50581 A1 | 8/2000 |
| WO | 01/29058 A1 | 4/2001 |
| WO | WO12013821 A1 * | 2/2012 |
| WO | 2012/054554 A2 | 4/2012 |

OTHER PUBLICATIONS

Parker et al. 2006; RDE-4 preferentially binds long dsRNA and its dimerization is necessary for cleavage of dsRNA to siRNA. RNA 12:807-818.*
Welker et al. 2007; Genes misregulated in C. elegans deficient in Dicer, RDE-4, or RCE-1 are enriched for innate immunity genes. RNA. 13: 1090-1102.*
Janus et al. 2009. Evidence for dicer-dependent RNA interference in the industrial penicillin producer Penicillium chrysogenum. Microbiology 15: 3946-3956.*
Zhang et al., "A host dicer is required for defective viral RNA production and recombinant virus vector RNA instability for a positive sense RNA virus," Proc. Natl. Acad. Sci. USA, 2008, vol. 105, No. 43, pp. 16749-16754.
Tabara et al., "The rde-1 gene, RNA interference and transposon siliencing in C. elegans," Cell, 1999, vol. 99, pp. 123-132.
Smith et al., "Comparison of Biosequences," Adv. Appl. Math., 1981, vol. 2, pp. 482-489.
Segers et al., "Evidence that RNA silencing functions as an antiviral defense mechanism in fungi," Proc. Natl. Acad. Sci. USA, 2007, vol. 104, No. 31, pp. 12902-12906.
Romano et al., "Quelling: transient inactivation of gene expression in Neurospora crassa by transformation with homologous sequences," Mol. Microbiol., 1992, vol. 6, pp. 3343-3353.
Penttila et al., "A versatile transformation system for the cellulolytic filamentous fungus Trichoderma reesei," Gene, 1987, vol. 61, pp. 155-164.
Pearson et al., "Improved tools for biological sequence comparison," Proc. Natl. Acad. Sci. USA, 1988, vol. 85, pp. 2444-2448.
PCT International Search Report and the Written Opinion of the International Searching Authority for International Application No. PCT/US2014/049159; ISA/EPO; dated Nov. 12, 2014.
Needleman et al., "A General Method Applicable to the Search for Similarities in the Amino Acid Sequence of Two Proteins," J. Mol. Biol., 1970, vol. 48, pp. 443-453.
Nakayashiki et al., "RNA silencing in fungi: Mechanisms and applications," FEBS Letters, 2005, vol. 579, No. 26, pp. 5950-5957.
McGinnis, "Use of Transgene-Induced RNAi to Regulate Endogenous Gene Expression," Methods in Molecular Biology: Transgenic Maize, 2009, vol. 526, pp. 91-99.
Li et al., "RNA interference pathways in filamentous fungi," Cell. Mol. Life Sci., 2010, vol. 67, pp. 3849-3863.

(Continued)

*Primary Examiner* — Karen Cochrane Carlson

(57) ABSTRACT

Described are methods for increasing the expression of a transgene in eukaryotic cells by reducing RNA interference (RNAi), and variant cells produce by the method. The methods and variant cells are useful, for example, for the efficient production of therapeutic and industrial polypeptides in eukaryotic cells.

13 Claims, 9 Drawing Sheets

Specification includes a Sequence Listing.

(56) References Cited

OTHER PUBLICATIONS

Lee et al., "Diverse pathways generate microRNA-like RNAs and Dicerindependent small interfering RNAs in fungi," Mol. Cell, 2010, vol. 38. No. 6, pp. 803-814.

Karlin et al., "Applications and statistics for multiple high-scoring segments in molecular sequences," Proc. Natl. Acad. Sci. USA, 1993, vol. 90, pp. 5873-5887.

Janus, et al., "Evidence for Dicer-dependent RNA interference in the industrial penicillin producer Penicillium chrysogenum,"Microbiology, 2009, vol. 155, pp. 3946-3956.

Higgins et al., "CLUSTAL: a package for performing multiple sequence alignment on a microcomputer," Gene, 1988, vol. 73, pp. 237-244.

Henikoff et al., "Amino acid substitution matrices from protein blocks," Proc. Natl. Acad. Sci. USA, 1992, vol. 89, pp. 10915-10919.

Fulci et al., "Quelling: post-transcriptional gene silencing guided by small RNAs in Neurospora crassa," Current Opinion in Microbiology, 2007, vol. 10, pp. 199-203.

Fire et al., "Potent and specific genetic interference by double-stranded RNA in Caenorhabditis elegans," Nature, 1998, vol. 391, pp. 806-811.

Feng et al., "Progressive Sequence Alignment as a Prerequisite to Correct Phylogenetic Trees," J. Mol. Evol. 1987, vol. 35, pp. 351-360.

Devereaux et al., "A comprehensive set of sequence analysis programs for the VAX," Nucleic Acids Res., 1984, vol. 12, pp. 387-395.

Cogoni et al., "Isolation of quelling defective (qde) mutants impaired in posttranscriptional transgene-induced gene silencing in Neurospora crassa," Proc. Natl. Acad. Sci. USA, 1997, vol. 94, No. 1, pp. 10233-10238.

Cogoni et al., "Gene silencing in Neurospora crassa requires a protein homologous to RNA-dependent RNA polymerase," Nature, 1999, vol. 399, pp. 166-169.

Brody et al., "RNAi-mediated gene silencing of highly expressed genes in the industrial fungi Trichoderma reesei and Aspergillus niger," Industrial Biotechnology, 2009, vol. 5, No. 1, pp. 53-60.

Altschul et al., "Local Alignment Statistics," Meth. Enzymol., 1993, vol. 266, pp. 460-480.

Altschul et al., "Basic Local Alignment Search Tool," J. Mol. Biol., 1990, vol. 215, pp. 403-410.

* cited by examiner

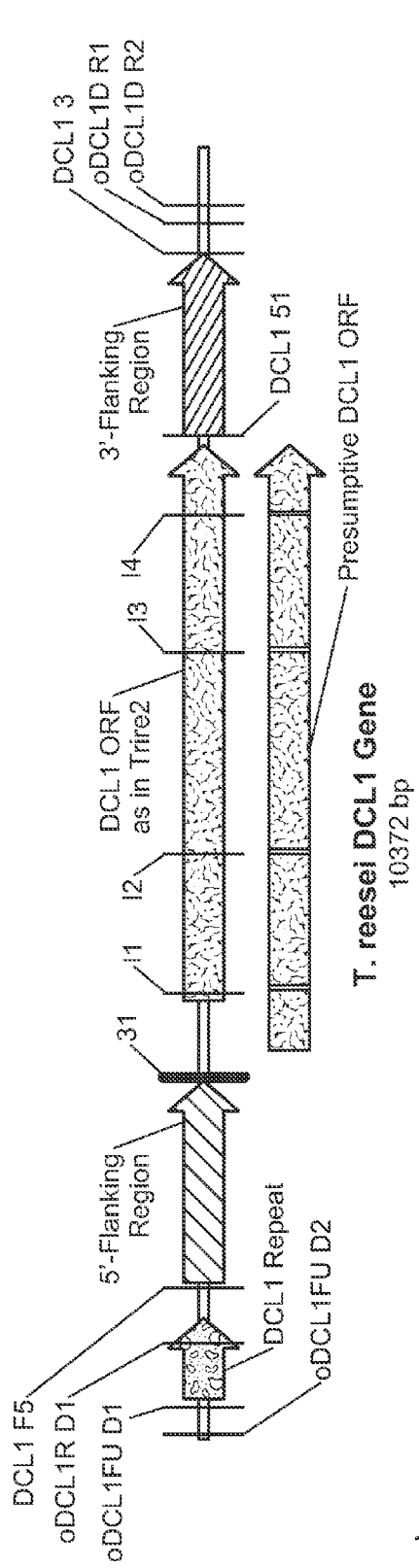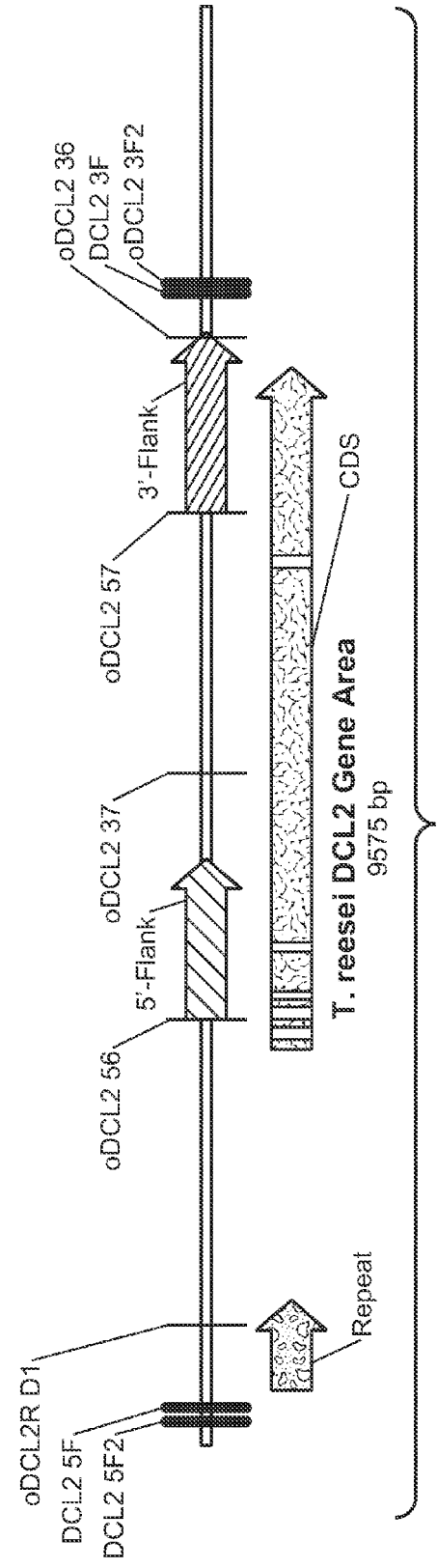
FIG. 2
FIG. 3

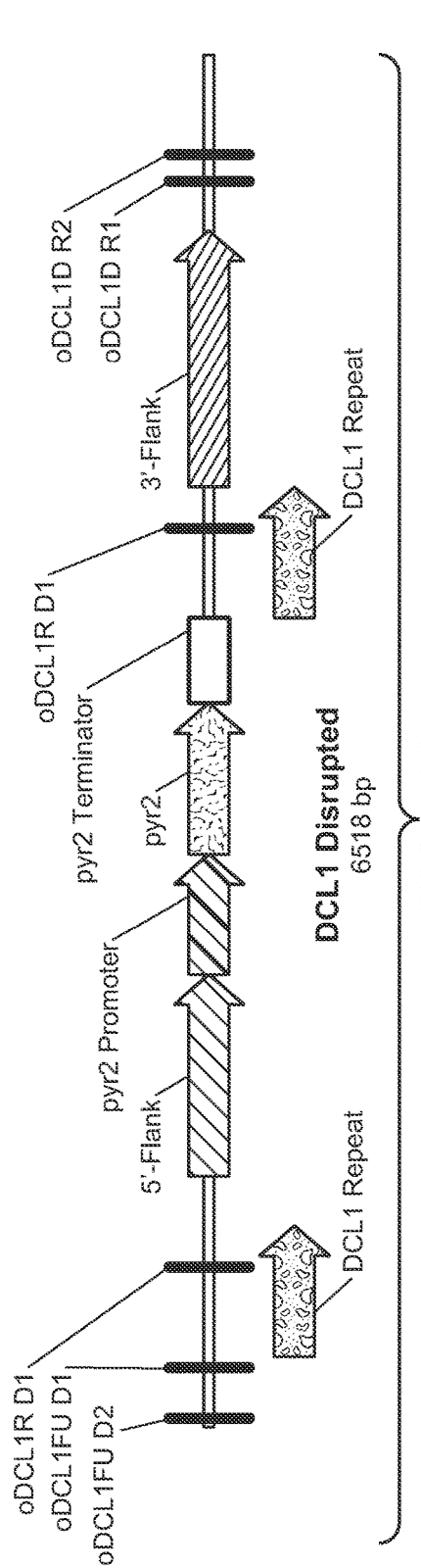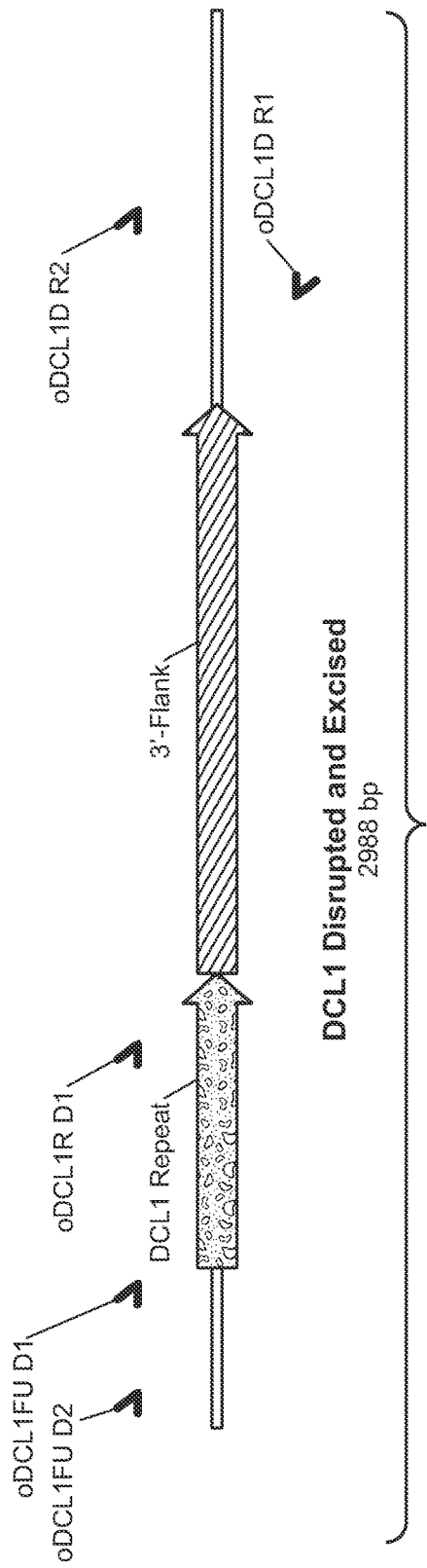
FIG. 4A
FIG. 4B

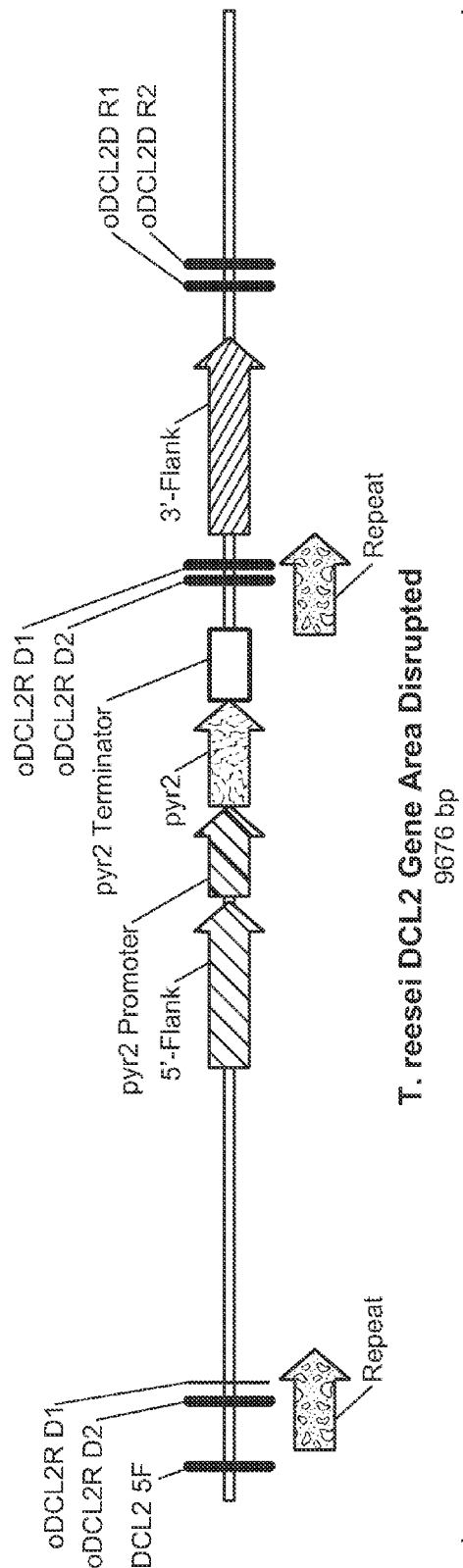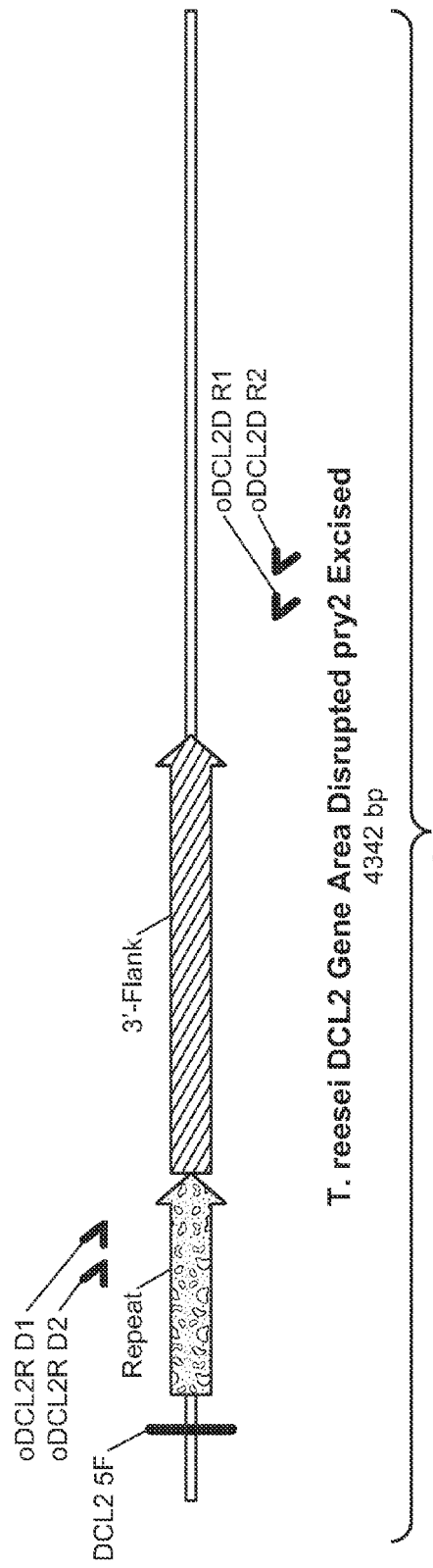
FIG. 5A
FIG. 5B

SEQUENCE LISTING

```
<160> NUMBER OF SEQ ID NOS: 30

<210> SEQ ID NO 1
<211> LENGTH: 36
<212> TYPE: DNA
<213> ORGANISM: Artificial Sequence
<220> FEATURE:
<223> OTHER INFORMATION: Synthetic primer: DCL1_3

<400> SEQUENCE: 1
cttacccaac gcgaacgatt gctagctctg ggctac                              36

<210> SEQ ID NO 2
<211> LENGTH: 50
<212> TYPE: DNA
<213> ORGANISM: Artificial Sequence
<220> FEATURE:
<223> OTHER INFORMATION: Synthetic primer: DCL1_31

<400> SEQUENCE: 2
ctgtgctagg tgacggctct ccttggtgcc agtatgcgaa gctttctttg              50

<210> SEQ ID NO 3
<211> LENGTH: 51
<212> TYPE: DNA
<213> ORGANISM: Artificial Sequence
<220> FEATURE:
<223> OTHER INFORMATION: Synthetic primer: DCL1_51

<400> SEQUENCE: 3
catactggca ccaaggagag ccgtcaccta gcacagggcc atacggacgg c            51

<210> SEQ ID NO 4
<211> LENGTH: 36
<212> TYPE: DNA
<213> ORGANISM: Artificial Sequence
<220> FEATURE:
<223> OTHER INFORMATION: Synthetic primer: DCL1_5

<400> SEQUENCE: 4
gcgcccagga agcagcggca acagcagcag caggag                             36

<210> SEQ ID NO 5
<211> LENGTH: 52
<212> TYPE: DNA
<213> ORGANISM: Artificial Sequence
<220> FEATURE:
<223> OTHER INFORMATION: Synthetic primer: DCL1R_5

<400> SEQUENCE: 5
ggtgtcgact ctagatcttc agcccattat tgctccaggc ggactggcca ag           52

<210> SEQ ID NO 6
<211> LENGTH: 37
<212> TYPE: DNA
<213> ORGANISM: Artificial Sequence
<220> FEATURE:
```

```
<223> OTHER INFORMATION: Synthetic primer: DCL1R_3

<400> SEQUENCE: 6
ctgtgggatc cagatttgga agacttgata cgggttc                              37

<210> SEQ ID NO 7
<211> LENGTH: 44
<212> TYPE: DNA
<213> ORGANISM: Artificial Sequence
<220> FEATURE:
<223> OTHER INFORMATION: Synthetic primer: oPYR2_35

<400> SEQUENCE: 7
ttgcaattga ctagtggatc caacgccggc tattaggcca taag                      44

<210> SEQ ID NO 8
<211> LENGTH: 40
<212> TYPE: DNA
<213> ORGANISM: Artificial Sequence
<220> FEATURE:
<223> OTHER INFORMATION: Synthetic primer: oPYR2_55

<400> SEQUENCE: 8
agtactagtc aattgctcga gtttataagt gacaacatgc                           40

<210> SEQ ID NO 9
<211> LENGTH: 38
<212> TYPE: DNA
<213> ORGANISM: Artificial Sequence
<220> FEATURE:
<223> OTHER INFORMATION: Synthetic primer: oDCL2_36

<400> SEQUENCE: 9
gttggatagg tacctagatg taagattcta tataagtc                             38

<210> SEQ ID NO 10
<211> LENGTH: 37
<212> TYPE: DNA
<213> ORGANISM: Artificial Sequence
<220> FEATURE:
<223> OTHER INFORMATION: Synthetic primer: DCL2_56

<400> SEQUENCE: 10
catcttcatc atcggcagcc cacgtaacct gtgccag                              37

<210> SEQ ID NO 11
<211> LENGTH: 55
<212> TYPE: DNA
<213> ORGANISM: Artificial Sequence
<220> FEATURE:
<223> OTHER INFORMATION: Synthetic primer: DCL2_57

<400> SEQUENCE: 11
caggcgaaag aggaggagat ctcaaaattc gtccccgaag gctcgtggac cagtg          55

<210> SEQ ID NO 12
<211> LENGTH: 56
<212> TYPE: DNA
<213> ORGANISM: Artificial Sequence
<220> FEATURE:
<223> OTHER INFORMATION: Synthetic primer: DCL2_37

<400> SEQUENCE: 12
ttcggggacg aattttgaga tctcctcctc tttcgcctgc cacttcaaga tcgcag         56
```

```
<210> SEQ ID NO 13
<211> LENGTH: 37
<212> TYPE: DNA
<213> ORGANISM: Artificial Sequence
<220> FEATURE:
<223> OTHER INFORMATION: Synthetic primer: DCL2_56

<400> SEQUENCE: 13
catcttcatc atcggcagcc cacgtaacct gtgccag                              37

<210> SEQ ID NO 14
<211> LENGTH: 55
<212> TYPE: DNA
<213> ORGANISM: Artificial Sequence
<220> FEATURE:
<223> OTHER INFORMATION: Synthetic primer: DCL2_57

<400> SEQUENCE: 14
caggcgaaag aggaggagat ctcaaaattc gtccccgaag gctcgtggac cagtg          55

<210> SEQ ID NO 15
<211> LENGTH: 42
<212> TYPE: DNA
<213> ORGANISM: Artificial Sequence
<220> FEATURE:
<223> OTHER INFORMATION: Synthetic primer: oDCL2R_3

<400> SEQUENCE: 15
ggttggatcc gcggaaaggt caataaaatg ggagttactg ag                        42

<210> SEQ ID NO 16
<211> LENGTH: 52
<212> TYPE: DNA
<213> ORGANISM: Artificial Sequence
<220> FEATURE:
<223> OTHER INFORMATION: Synthetic primer: oDCL2R_5

<400> SEQUENCE: 16
ggttgtcgac tctagatctg ccctgtccag catcgagctg acctctctat tg             52

<210> SEQ ID NO 17
<211> LENGTH: 36
<212> TYPE: DNA
<213> ORGANISM: Artificial Sequence
<220> FEATURE:
<223> OTHER INFORMATION: Synthetic primer: oDCL1D_R1

<400> SEQUENCE: 17
cagactcgga cgtcgactcc tttcgtggca agtatc                               36

<210> SEQ ID NO 18
<211> LENGTH: 36
<212> TYPE: DNA
<213> ORGANISM: Artificial Sequence
<220> FEATURE:
<223> OTHER INFORMATION: Synthetic primer: oDCL1D_R2

<400> SEQUENCE: 18
gggagatgat tcttgcggcg aatccatctt catctc                               36

<210> SEQ ID NO 19
<211> LENGTH: 36
<212> TYPE: DNA
<213> ORGANISM: Artificial Sequence
<220> FEATURE:
<223> OTHER INFORMATION: Synthetic primer: oDCL1FU_D1
```

<400> SEQUENCE: 19
ccatgtcatt tcaccagaga cagcaaatgt cggaag                36

<210> SEQ ID NO 20
<211> LENGTH: 37
<212> TYPE: DNA
<213> ORGANISM: Artificial Sequence
<220> FEATURE:
<223> OTHER INFORMATION: Synthetic primer: oDCL1FU_D2

<400> SEQUENCE: 20
ccatcaagaa gattgaggag gccatcaaag acctcgg                37

<210> SEQ ID NO 21
<211> LENGTH: 36
<212> TYPE: DNA
<213> ORGANISM: Artificial Sequence
<220> FEATURE:
<223> OTHER INFORMATION: Synthetic primer: oDCL1R_D1

<400> SEQUENCE: 21
gagcgcttta tgacaagcaa tgacagaggg caactg                36

<210> SEQ ID NO 22
<211> LENGTH: 36
<212> TYPE: DNA
<213> ORGANISM: Artificial Sequence
<220> FEATURE:
<223> OTHER INFORMATION: Synthetic primer: oDCL2_5F

<400> SEQUENCE: 22
ctaatttcag tattctaggt catgctacgc aataac                36

<210> SEQ ID NO 23
<211> LENGTH: 38
<212> TYPE: DNA
<213> ORGANISM: Artificial Sequence
<220> FEATURE:
<223> OTHER INFORMATION: Synthetic primer: oDCL2D_R1

<400> SEQUENCE: 23
ccaatcaaac accaccacca ctcagaatct gcatcctc                38

<210> SEQ ID NO 24
<211> LENGTH: 38
<212> TYPE: DNA
<213> ORGANISM: Artificial Sequence
<220> FEATURE:
<223> OTHER INFORMATION: Synthetic primer: oDCL2D_R2

<400> SEQUENCE: 24
ccagccaacc ctcgactcaa aagaagacca aaactccg                38

<210> SEQ ID NO 25
<211> LENGTH: 38
<212> TYPE: DNA
<213> ORGANISM: Artificial Sequence
<220> FEATURE:
<223> OTHER INFORMATION: Synthetic primer: oDCL2R_D1

<400> SEQUENCE: 25
gtgcattaat tagtcactgc taccaatggt gattcctg                38

<210> SEQ ID NO 26
<211> LENGTH: 38

```
<212> TYPE: DNA
<213> ORGANISM: Artificial Sequence
<220> FEATURE:
<223> OTHER INFORMATION: Synthetic primer: oDCL2R_D2

<400> SEQUENCE: 26
gaaggtgatg atgacggtct gcctacatac cttagatc                          38

<210> SEQ ID NO 27
<211> LENGTH: 42
<212> TYPE: DNA
<213> ORGANISM: Artificial Sequence
<220> FEATURE:
<223> OTHER INFORMATION: Synthetic primer: oCBHT_3

<400> SEQUENCE: 27
tggtactggg atacacgaag agcggcgatt ctacgggtta tg                     42

<210> SEQ ID NO 28
<211> LENGTH: 39
<212> TYPE: DNA
<213> ORGANISM: Artificial Sequence
<220> FEATURE:
<223> OTHER INFORMATION: Synthetic primer: oTrex3_AmdS_3

<400> SEQUENCE: 28
ctagactgga aacgcaaccc tgaagggatt cttcctttg                         39

<210> SEQ ID NO 29
<211> LENGTH: 37
<212> TYPE: DNA
<213> ORGANISM: Artificial Sequence
<220> FEATURE:
<223> OTHER INFORMATION: Synthetic primer: oTrex3_AMP_5

<400> SEQUENCE: 29
gtatagtaat acgagtcgca tctaaatact ccgaagc                           37

<210> SEQ ID NO 30
<211> LENGTH: 41
<212> TYPE: DNA
<213> ORGANISM: Artificial Sequence
<220> FEATURE:
<223> OTHER INFORMATION: Synthetic primer: oTrex8_Pyr2_3

<400> SEQUENCE: 30
ggaggggacg atacacgcac catggacccc agtggggaag c                      41
```

INCREASING THE EXPRESSION OF A TRANSGENE IN EUKARYOTIC CELLS BY REDUCING RNA INTERFERENCE

PRIORITY

The present patent application is the National Stage of International Application No. PCT/US2014/049159, filed Jul. 31, 2014, which claims priority to U.S. Provisional Patent Application No. 61/863,829, filed on Aug. 8, 2013, which are hereby incorporated by reference in their entirety.

SEQUENCE LISTING

The sequence listing submitted via EFS, in compliance with 37 C.F.R. § 1.52(e), is incorporated herein by reference. The sequence listing text file submitted via EFS contains the file "NB31613-US-PCT_SequenceListing.txt" created on May. 9, 2016, which is 6,329 bytes in size.

TECHNICAL FIELD

Described are methods for increasing the expression of a transgene in eukaryotic cells by reducing RNA interference (RNAi), and variant cells produced by the method. The methods and variant cells are useful, for example, for the efficient production of therapeutic and industrial polypeptides in eukaryotic cells.

REFERENCES

The following references, and additional reference cited herein, are hereby incorporated by reference:

Fire, A. et al. (1998). *Nature* 391:806-11.
Fulci, V. and Macino, G. (2007) *Current Opinion in Microbiology* 10:199-203.
Janus, D. et al. (2009) *Microbiology* 155:3946-56.
Nakayashiki, H. (2005) *FEBS Letters* 579:5950-57.
Brody, H. and Maiyuran, S. (2009) *Industrial Biotechnology* 5:53-60.
McGinnis, K. (2009) *Methods in Molecular Biology: Transgenic Maize* 526:91-99.

BACKGROUND

RNA interference (RNAi) is a phenomenon by which RNA molecules inhibit gene expression. RNAi occurs when a mRNA, typically transcribed from a transgene, is converted into double-stranded RNA (dsRNA) by an RNA-dependent RNA polymerase (RdRP). The dsRNA becomes a substrate for Dicer-like proteins, which cut the dsRNA into small interfering dsRNAs (siRNA) about 25 nucleotides or shorter in length. The siRNA becomes incorporated into an RNA-induced silencing complex (RISC), which targets and degrades additional transgene mRNA in a sequence-specific manner based on the sequence of the particular siRNA. The result is reduced expression of the transgene, as well as endogenous genes having sufficiently similar nucleotide sequences to that transgene. The phenomenon was first described by Fire and Mello in *Caenorhabditis elegans* (Fire, A. et al. (1998). *Nature* 391:806-11).

RNAi occurs in a wide variety of eukaryotic cells, and is known by a number of different names, including co-suppression, post transcriptional gene silencing (PTGS), and quelling. Quelling is the term usually reserved for RNAi in fungal molecular biology. Some fungi can have a strong quelling response, while other have a weak response, or no quelling response at all. Quelling was first described in Neurospora in the early 1990s (Romano, N. et al. (1992) *Mol. Microbiol.* 6:3343-53).

SUMMARY

Described is a method for increasing the expression level of a transgene in eukaryotic cells by introducing a genetic alteration into the cells that reduces the amount of RNA interference (RNAi). Aspects and embodiments of the present methods and variant cells are summarized in the following separately-numbered paragraphs:

1. In one aspect, a method for increasing the expression level of a transgene in eukaryotic cells is provided, comprising introducing a genetic alteration into the cells, which genetic alteration reduces the amount of RNA interference in the cells compared to the amount of RNA interference in the absence of the genetic alteration.

2. In some embodiments of the method of paragraph 1, the genetic alteration reduces or prevents the formation or dsRNA and/or siRNA in the cells.

3. In some embodiments of the method of paragraphs 1 or 2, the genetic alteration comprises a disruption of a Dicer-like gene.

4. In some embodiments of the method of paragraphs 1 or 2, the genetic alteration comprises a disruption of an RNA-dependent RNA polymerase. 5. In some embodiments of the method of paragraphs 3 or 4, the disruption of the gene is the result of mutagenesis of the gene.

6. In some embodiments of the method of paragraphs 3-5, the disruption of the gene is performed using site-specific recombination.

7. In some embodiments of the method of paragraphs 3-6, the disruption of the gene is performed in combination with introducing a selectable marker at the genetic locus of the gene.

8. In some embodiments of the method of paragraphs 3-7, the disruption of the gene is performed in combination with introducing a transgene encoding a protein of interest.

9. In some embodiments of the method of paragraphs 1-8, the cells produces substantially the same amount of total protein per unit amount of biomass compared to the amount of protein per unit amount of biomass produced by equivalent cells lacking the genetic alteration.

10. In some embodiments of the method of paragraphs 1-9, wherein the eukaryotic cells are plant cells, animal cells, insect cells, or fungal cells.

11. In some embodiments of the method of paragraphs 1-9, the eukaryotic cells are filamentous fungus cells.

12. In some embodiments of the method of paragraph 10, the eukaryotic cells are Pezizomycotina species cells.

13. In some embodiments of the method of paragraph 11, the filamentous fungus is *Trichoderma reesei*.

14. In some embodiments, the method of paragraphs 1-7 or 9-13 further comprises introducing a transgene for expressing a protein of interest into the cells.

15. In some embodiments, the method of paragraphs 8 or 14 further comprises introducing an additional copy of the transgene into the cells, wherein the levels of expression of the transgene after introducing the additional copy of the transgene into the cells is no lower than the levels of expression of the transgene before introducing the additional copy of the transgene into the cells. In the case of the embodiment of paragraph 8, the additional copy of the transgene mentioned in this paragraph is in addition to the transgene mentioned in paragraph 8.

16. In some embodiments of the method of paragraphs 14 or 15, the transgene encoding the protein of interest is present in the cells prior to introducing the genetic alteration that reduces or prevents RNA interference.

17. In some embodiments of the method of paragraphs 14 or 15, the transgene encoding the protein of interest is introduced into the cells after introducing the genetic alteration that reduces or prevents RNA interference.

18. In another aspect, a method for screening transformed or transfected cells for cells that highly express a transgene is provided, comprising introducing a genetic alteration into the cells, which genetic alteration reduces the amount of RNA interference in the cells compared to the amount of RNA interference in the absence of the genetic alteration, and further introducing a transgene into the cells, wherein the genetic alteration increases the average expression levels of a protein encoded by the transgene in the transformed or transfected cells, thereby allowing the screening of fewer transformed or transfected cells for the purposes of identifying cells that highly express the protein encoded by the transgene, compared to the number of transformed or transfected cells that must be screened when the cells do not comprise the genetic alteration. The embodiments described in any of paragraphs 2-13 and 15-17 can be used in combination with the method of paragraph 18.

19. In another aspect, a method for increasing the expression level of a transgene in eukaryotic cells is provided, comprising introducing the transgene at a locus of a gene associated with RNA interference, wherein introducing the transgene disrupts the gene associated with RNA interference and reduces the amount of RNA interference in the cells, thereby increasing the expression level of the transgene compared to that in cells where the gene associated with RNA interference is intact. The embodiments described in any of paragraphs 2-7, 9-13, and 15-17 can be used in combination with the method of paragraph 18.

20. In another aspect, a eukaryotic cell produced by the method of any of claims 1-19 is provided.

21. In another aspect, a protein of interest produced by the method of any of claims 1-19 is provided.

22. In another aspect, variant eukaryotic cells derived from parental eukaryotic cells are provided, the variant cells comprising a genetic alteration that causes the variant cells to exhibit reduced RNA interference compared to the parental cells, wherein the variant cells are capable of producing higher levels of a protein of interest encoded by a transgene, and/or where the variant cells have higher average expression levels of a protein of interest encoded by a transgene following transformation of the transgene, compared to the parental cells, wherein the variant cells produces substantially the same amount of protein per unit amount of biomass compared to the amount of protein per unit amount of biomass produced by equivalent cells lacking the genetic alteration.

23. In some embodiments of the variant cells of paragraph 22, the genetic alteration is the disruption of a gene encoding a protein involved with RNA interference.

24. In some embodiments of the variant cells of paragraph 23, the genetic alteration comprises a disruption of a gene encoding a Dicer-like protein.

25. In some embodiments of the variant cells of paragraph 23, the genetic alteration comprises a disruption of a gene encoding an RNA-dependent RNA polymerase.

26. In some embodiments of the variant cells of paragraphs 23-25, the disruption is the mutagenesis of the gene.

27. In some embodiments of the variant cells of paragraphs 23-25, the disruption is the partial or complete deletion of the gene.

28. In some embodiments of the variant cells of paragraphs 23-27, the disruption of the gene is performed using site-specific recombination.

29. In some embodiments of the variant cells of paragraphs 23-28, the disruption of the gene is performed in combination with introducing a selectable marker at the genetic locus of the gene.

30. In some embodiments, the variant cells of any of paragraphs 22-29, further comprise a transgene encoding a protein of interest.

31. In some embodiments, the variant cells of any of paragraphs 22-29 further comprise a plurality of copies of a transgene encoding a protein of interest.

These and other aspects and embodiments of present methods and variant cells will be apparent from the description, including the appended Examples and accompanying Figures.

BRIEF DESCRIPTION OF THE DRAWINGS

FIG. 2 is a schematic of the chromosomal region of *T. reesei* containing the dcl1 gene. The two dcl1 flanking regions and the dcl1 repeat region are indicated. The ORF corresponding to protein ID 69494 in the Trire 2.0 database and the presumptive corrected ORF with a 5'-terminal extension to the nearest ATG codon are shown. Annealing loci for amplification primers are indicated.

FIG. 3 is a schematic of the chromosomal region of *T. reesei* containing the dcl2 gene. The two dcl2 flanking regions and the dcl2 repeat region are indicated. The ORF corresponding to protein ID 79823 in the Trire 2.0 database is shown as well. Annealing loci for amplification primers are indicated.

FIGS. 4A and 4B are schematics of the dcl1 chromosomal region of *T. reesei* after gene disruption (4A) and after excision of the pyr2 marker gene (4B). Annealing loci for the primers used to mapping the deletions are indicated.

FIGS. 5A and 5B are schematics of the dcl2 chromosomal region of *T. reesei* after gene disruption (5A) and after excision of the pyr2 marker gene (5B). Annealing loci for the primers used to mapping the deletions are indicated.

DETAILED DESCRIPTION

I. Overview

Figure 1:
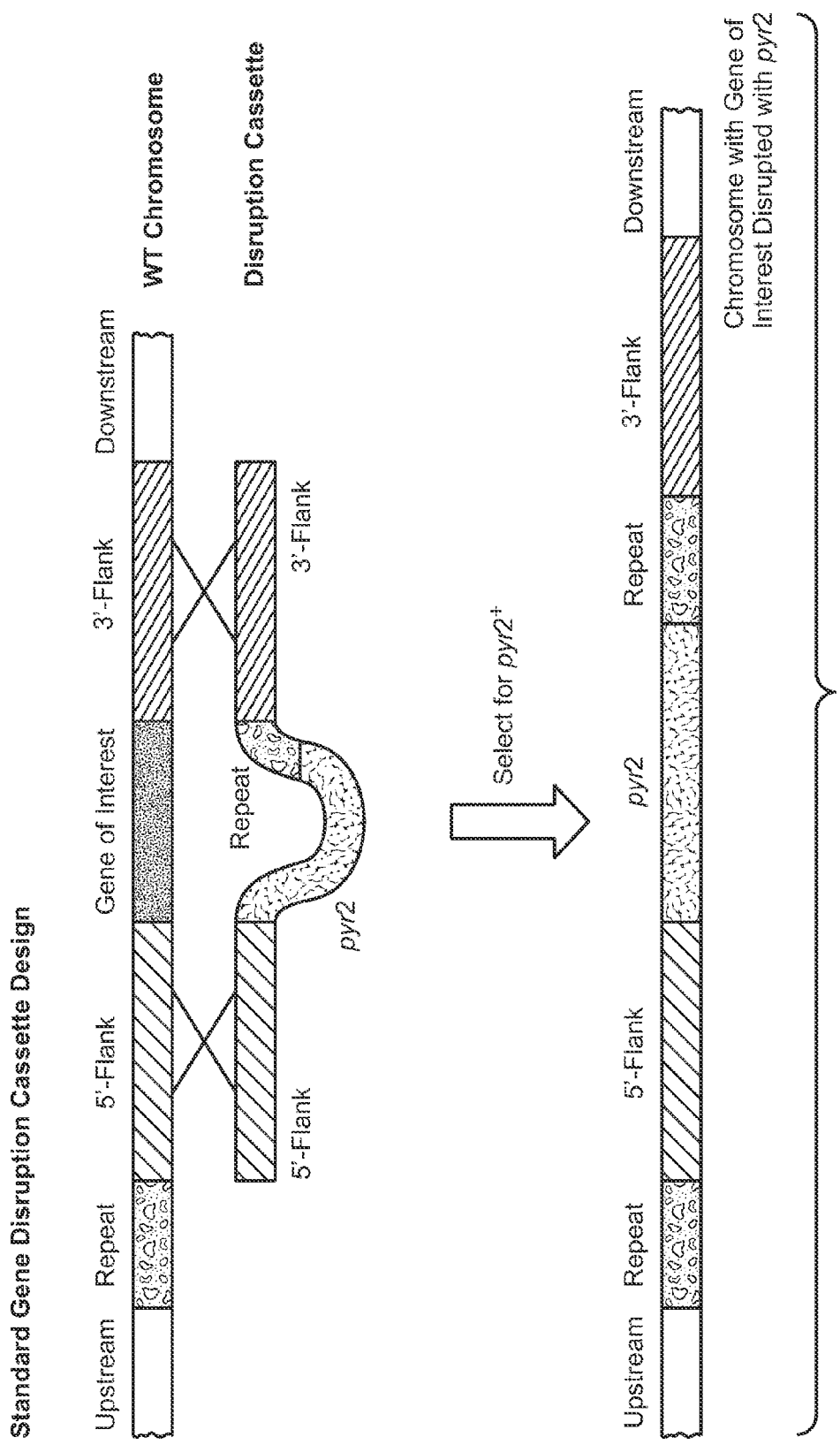
FIG. 1 is a schematic of a standard-design disruption cassette. In *T. reesei*, the length of the 5' and 3'-flanking regions are 1-1.5 kb, and the length of the repeat region is 0.5-0.7 kb.

Described are methods for increasing the expression of transgenes in eukaryotic cells by disrupting their RNA interference (RNAi) mechanism, and strains of cells produced by such a method. While the RNAi mechanism has been studied in eukaryotic cells for some years, and RNAi has been used to intentionally silence unwanted gene expression, disrupting RNAi to improve the expression of transgenes has heretofore not been described. The present methods and cells are useful for expressing any number of industrial and pharmaceutical proteins of interest.

II. Definitions

Prior to describing the present strains and methods in detail, the following terms are defined for clarity. Terms not defined should be accorded their ordinary meanings as used in the relevant art.

As used herein, the term "RNA interference," abbreviated "RNAi," broadly refers to an RNA-mediated gene silencing mechanism in eukaryotic cells. RNAi results in reduced expression of a subset of proteins expressed within a eukaryotic cell. RNAi is also referred to as "co-suppression" in the field of plant molecular biology and "quelling" in the field of fungal molecular biology. RNAi is described in detail in the reference cited herein.

As used herein, the term "quelling" refers to RNA-mediated gene silencing in fungi. Quelling is described in detail in the reference cited herein.

As used herein, a "transgene" is an exogenous gene that is introduced into a host organism. Transgenes may be introduced by transfection, transformation, transduction, or infection, and are preferably integrated into the host cell chromosome. Transgenes typically encode proteins of interest, such as industrially or pharmaceutically important proteins. A transgene may encode a protein that is not normally expressed by the host cell or that is normally expressed by the host cell. In the latter case, the transgene may even be the same as a gene naturally present in the host cell. Nonetheless, transgenes are exogenous and must be introduced to host cells by genetic manipulation.

As used herein, the terms "wild-type" is to refer to genes, proteins, or cells found in nature.

As used herein, the terms "variant," "variant cell," "variant strain," and similar expressions, refer to a eukaryotic cell that has been genetically altered.

As used herein, the phrase "substantially free of an activity," or similar phrases, means that a specified activity is either undetectable in an admixture or present in an amount that would not interfere with the intended purpose of the admixture.

As used herein, the terms "polypeptide" and "protein" are used interchangeably to refer to polymers of any length comprising amino acid residues linked by peptide bonds. The conventional one-letter or three-letter codes for amino acid residues are used herein. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, the term "derivative polypeptide/protein" refers to a protein which is derived or derivable from a protein by addition of one or more amino acids to either or both the N- and C-terminal end(s), substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. The preparation of a protein derivative may be achieved by modifying a DNA sequence which encodes for the native protein, transformation of that DNA sequence into a suitable host, and expression of the modified DNA sequence to form the derivative protein.

As used herein, the term "variant proteins" refers to proteins that differ from a reference/parental protein (e.g., a wild-type protein) by substitutions, deletions, and/or insertions at small number of amino acid residues. The number of differing amino acid residues between the variant and parental protein may be one or more, for example, 1, 2, 3, 4, 5, 6, 7, 8, 9, 10, 15, 20, 30, 40, 50, or more amino acid residues. Variant proteins may share at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with a reference protein. A variant protein may also differ from a reference protein in selected motifs, domains, epitopes, conserved regions, and the like.

As used herein, the term "homologous protein," or simply "homolog" refers to a protein that has similar activity and/or structure to a reference protein. It is not intended that homologs necessarily be evolutionarily related, although this is often the case. Homologs typically have a similar structure and can be identified by primary sequence analysis, secondary or tertiary structure analysis, functional analysis, and/or immunological cross-reactivity.

The degree of homology between sequences may be determined using any suitable method known in the art (see, e.g., Smith and Waterman (1981) *Adv. Appl. Math.* 2:482; Needleman and Wunsch (1970) *J. Mol. Biol.,* 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, Wis.); and Devereux et al. (1984) *Nucleic Acids Res.* 12:387-95). For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'5, N'–4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Sequence identity may be determined using known programs such as BLAST, ALIGN, and CLUSTAL using standard parameters. (See, e.g., Altschul, et al. (1990) *J. Mol. Biol.* 215:403-410; Henikoff et al. (1989) *Proc. Natl. Acad. Sci. USA* 89:10915; Karin et al. (1993) *Proc. Natl. Acad. Sci USA* 90:5873; and Higgins et al. (1988) *Gene* 73:237-244). Software for performing BLAST analyses is publicly available through the National Center for Biotechnology Information. Also, databases may be searched using FASTA (Pearson et al. (1988) *Proc. Natl. Acad. Sci. USA* 85:2444-48). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent promoter and/or terminator sequences.

As used herein, "disruption of a gene" refers broadly to any genetic or chemical manipulation that substantially prevents a cell from producing a function gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product.

As used herein, "genetic manipulation" refers to the alteration of a preselected nucleic acid target sequence, e.g., using macromolecules (i.e., enzymes and/or nucleic acids) that preferentially act on the preselected nucleic acid sequence. In this manner genetic manipulation is distinct from chemical manipulation, in which small molecules are used to randomly affect changes to a nucleic acid sequence that is not preselected.

As used herein, a "genetic alteration" is a change in the DNA of a cell that results from genetic manipulation, and is distinct from a change in the DNA of a cell that results from chemical manipulation.

As used herein, a "primarily genetic determinant" refers to a gene, or genetic manipulation thereof, that is necessary and sufficient to confer a specified phenotype in the absence of other genes, or genetic manipulations, thereof.

As used herein, a "functional polypeptide/protein" is a protein that posses an activity, such as an enzymatic activity, a binding activity, a surface-active property, or the like, and which has not been mutagenized, truncated, or otherwise modified to abolish or reduce that activity. Functional polypeptides may be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product.

As used herein, variant cells (or a variant strain) "maintain or retain a high level of protein expression and/or secretion" compared to parental cells (or a parental strain) if the difference in protein expression between the variant cells and a parental cells is less than about 20%, less than about 15%, less than about 10%, less than about 7%, less than about 5%, or even less than about 3%.

As used herein, a "protein of interest" is a protein that is desired to be produced in a host cells. Generally, proteins of interest are commercially important for industrial or pharmaceutical use, making them desirable to produce in large quantities. Proteins of interest are to be distinguished from myriad other proteins expressed by the filamentous fungus cells, which are generally not of interest as products and are mainly considered background protein contaminants.

As used herein, variant cells (or a variant strain) produce(s) "substantially the same amount" of protein per unit amount of biomass as parental cells (or a parental strain) if the amount of protein produced by the variant cells is no more than 20% reduced, no more than 15% reduced, no more than 10% reduced, an even no more than 5% reduced compared to the amount of protein produced by the parental cells, wherein the amount of protein is normalized to the total amount of biomass of cells from which protein production is measured, wherein biomass may be expressed in terms of either wet (e.g., of cell pellet) or dry weight.

As used herein, the amount of protein of interest expressed by variant cells and parental cells is "substantially similar" if the difference in expression between the variant cells and the parental cells is less than about 20%, less than about 15%, less than about 10%, less than about 5%, less than about 4%, less than about 3%, less than about 2%, or even less than about 1%.

As used herein, the singular articles "a," "an," and "the" encompass the plural referents unless the context clearly dictates otherwise. All references cited herein are hereby incorporated by reference in their entirety. The following abbreviations/acronyms have the following meanings unless otherwise specified:

| | |
|---|---|
| EC | enzyme commission |
| kDa | kiloDalton |
| kb | kilobase |
| MW | molecular weight |
| w/v | weight/volume |
| w/w | weight/weight |
| v/v | volume/volume |
| wt % | weight percent |
| ° C. | degrees Centigrade |
| $H_2O$ | water |
| $H_2O_2$ | hydrogen peroxide |
| $dH_2O$ or DI | deionized water |
| $dIH_2O$ | deionized water, Milli-Q filtration |
| g or gm | gram |
| μg | microgram |
| mg | milligram |
| kg | kilogram |
| lb | pound |
| μL and μl | microliter |
| mL and ml | milliliter |
| mm | millimeter |
| μm | micrometer |
| M | molar |
| mM | millimolar |
| μM | micromolar |
| U | unit |
| ppm | parts per million |
| sec and " | second |
| min and ' | minute |
| hr | hour |
| EtOH | ethanol |
| eq. | equivalent |
| N | normal |
| PCR | polymerase chain reaction |
| SDS-PAGE | sodium dodecyl sulfate polyacrylamide gel electrophoresis |
| DNA | deoxyribonucleic acid |
| RNA | ribonucleic acid |
| FOA | fluoroorotic acid |
| ATP | adenosine-5'-triphosphate |
| UV | ultraviolet |
| AAPN | Ala-Ala-Phe-p-nitroanilide |
| $A_{540}$ | absorbance measured at a wavelength of 540 nm |
| CMC | carboxymethyl cellulose |
| rpm | revolutions per minute |
| Δ | relating to a deletion |
| RNAi | RNA interference |
| PTGS | post transcriptional gene silencing |
| dsRNA | double-stranded RNA |
| RdRP | RNA-dependent RNA polymerase |
| siRNA | small interfering dsRNA |
| POI | protein(s) of interest |
| PPD | PAZ piwi domain |
| DOE | Department of Energy |
| JGI | Joint Genome Institute |
| APY | aminopeptidase Y |
| 3PP | aminopeptidyl tripeptidases |
| CBH1 | cellobiohydrolase 1 |
| CBH2 | cellobiohydrolase 2 |

III. Increasing Transgene Expression by Disrupting the RNAi Mechanism

Described is a method for increasing the expression level of a transgene in eukaryotic cells by introducing a genetic alteration into the cells that reduces the amount of RNA interference (RNAi). Also described are cells produced by such a method. While exploiting RNAi to decrease gene expression has been described, disrupting RNAi to increase the expression of a transgene is heretofore unknown. It has now been observed that cells deficient for RNAi make excellent production hosts for the high level expression of proteins of interest (POI) encoded by transgenes, including increasing the maximum levels of expression in cells, increasing the average level or expression in a plurality of transformants, and overcoming the decrease in expression that is sometime observed when multiple copies of a transgene are introduced into cells. Cells with disrupted RNAi do not appear to suffer from growth defects, at least not over the course of a submerged culture batch fermentation.

Disruption of the RNAi mechanism can be accomplished by making one or more genetic alterations that disrupt one or more genes associated with the RNAi mechanism. Exemplary genes include qde-1, which encodes a cellular RNA-dependent RNA polymerase (RdRP), qde-2 which encodes an Argonaute or PAZ piwi domain (PPD) protein, qde-3 which encodes a RecQ DNA helicase, qip which encodes a QDE-2-interacting exonuclease, and dcl-1 and dcl-2, which encode Dicer-like proteins involved in the processing of dsRNA molecules to yield siRNAs of about 21-25 nucleotides in length in an ATP-dependent manner. The Dicer proteins appear to have partially redundant functions in some organisms. Homologs of these genes have been identified in a variety or organisms, including filamentous fungi, mammalian cells, plant cells, and insect cells. Further homologs can be identified by amino acid sequence alignment and other well-established bioinformatic techniques.

Disruption of one or more of these genes can be performed using any suitable method that substantially prevents expression of a function protein encoded by the one or more genes. Exemplary methods of disruption include complete or partial deletion of a gene, including complete or partial deletion of, e.g., the coding sequence, the promoter, the terminator, an enhancer, or another regulatory element. Disruption of a gene can also be performed by the complete or partial deletion of a portion of the chromosome that includes any portion of the gene. Disrupting a gene can also be performed by making nucleotide substitutions or insertions in any portion of the gene, e.g., the coding sequence, the promoter, the terminator, an enhancer, or another regulatory element. Preferably, deletions, insertions, and/or substitutions (collectively referred to as mutations) are made by genetic manipulation using sequence-specific molecular biology techniques, although they can also be made by chemical mutagenesis.

Mutations in a gene may reduce the efficiency of the promoter, reduce the efficiency of an enhancer, interfere with the splicing or editing of the mRNA, interfere with the translation of the mRNA, introduce a stop codon into the coding sequence to prevent the translation of full-length protein, change the coding sequence of the protein to produce a less active or inactive protein or reduce protein interaction with other cell components, change the coding sequence of the protein to produce a less stable protein or target the protein for destruction, cause the protein to misfold or be incorrectly modified (e.g., by glycosylation), or interfere with cellular trafficking of a protein. Generally, the goal of these and other genetic manipulations is to reduce or prevent the expression of a functional RNAi-associated protein, or reduce or prevent the normal biological activity of such proteins.

Exemplary methods for disrupting a gene include site-specific recombination, targeted insertion, the use of transposable elements, transduction by viruses, and chemical mutagenesis. Gene disruption may be accompanied by the simultaneous or sequential insertion of, e.g., a selectable marker, a fluorescent or other distinguishable marker, a cloning site or cloning cassette, a sequence fingerprint to allow subsequent identification of the strain, or other genetic modification to add distinctiveness or functionality to the resulting cells.

The cells in which the RNAi mechanism is disrupted may already comprise one or more copies of a transgene of interest desired to be expressed at high levels. Alternatively, one or more copies of a transgene of interest may be introduced to cells after the RNAi mechanism is disrupted. In a further alternative, one or more copies of a transgene of interest may be introduced in the process of disrupting a gene associated with RNAi. In this manner, the present methods contemplate the integration of a transgene at the site of a gene associated with RNAi, thereby simultaneously adding the trangene to the chromosome of a cell while disrupting the RNAi mechanism.

Eukaryotic cells in which the RNAi mechanism may be disrupted include cells derived from humans, monkeys and rodents, such as Chinese hamster ovary (CHO) cells, NIH/3T3 cells, COS cells, 293 cells, and VERO cells, insect cells, such as *Drosophila* and lepidopteran cells, plant cells such as tobacco, corn, rice, algae and lemna cells, and fugal cells, such as yeast and filamentous fungal cells. Exemplary filamentous fungus cells are from the phylum Ascomycota, subphylum Pezizomycotina, particularly those that have a vegetative hyphae state. Particular exemplary fungal cells are those used for the production of commercially important industrial and pharmaceutical proteins, including, but not limited to *Schizosaccharomyces* spp., *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., *Myceliophthora* spp., and *Neurospora* spp. Particular organisms include, but are not limited to, *Trichoderma reesei* (previously classified as *Trichoderma longibrachiatum* and *Hypocrea jecorina*), *Aspergillus niger*, *Aspergillus fumigatus*, *Aspergillus itaconicus*, *Aspergillus oryzae*, *Aspergillus nidulans*, *Aspergillus terreus*, *Aspergillus sojae*, *Aspergillus japonicus*, *Scedosporium prolificans*, *Neurospora crassa*, *Penicillium funiculosum*, *Penicillium chrysogenum*, *Talaromyces (Geosmithia) emersonii*, *Fusarium venenatum*, *Myceliophthora thermophila*, and *Chrysosporium lucknowense*.

The present methods and variant cells have numerous applications. They can be used increase expression levels of a trangene in production organisms for the purposes of increasing yields and relative purity when making industrial or pharmaceutical proteins. They can reduce the time required to identify high level expressing cells following transfection, transformation, or transduction with a transgene. They can shorter the time required to identify a high-level expressing production hosts. They can reduce the problems associated with multiple copies of transgenes, which can significantly reduce protein expression in some host organisms. They can be used to increase the expression of a transgene in cells, where the increases in the amount of protein encoded by the transgene produces an increased amount of a metabolite of interest.

These and other aspects and embodiments of the present methods and variant cells will be apparent to the skilled person in view of the foregoing description and appended examples.

EXAMPLES

Example 1

Construction of a *T. reesei* Strain with Disrupted dcl1 and dcl2 Genes

A. Identification of the Dicer Genes in *T. reesei*

Strain DURA ΔEG5 18 has been described (WO2012/054554 and US2012107872). A derivative of this strain, named 653MU, was used as the starting point for this example. Compared to DURA ΔEG5 18, 653MU contains three additional deletions (the two cellulase genes, egl3 and egl6, as well the mannanase gene, man1). 653MU lacks a functional pyr2 gene (encoding orotate phosphoribosyltransferase). None of these deletions are of any significance to the present methods or variant cells.

*T. reesei* genes encoding two presumptive Dicer-like enzymes were identified in the Department of Energy (DOE) Joint Genome Institute (JGI) database based on homology searches using the sequences of the Neurospora crassa DCL1 and DCL2 proteins, encoded by the dcl1 and dcl2 genes, respectively. Protein ID 69494 in Trire 2.0 shows the highest homology to the *N. crassa* DCL1 protein and is herein referred to as the *T. reesei* DCL1 protein, with the gene encoding it being referred to as dcl1. According to the JGI annotation, protein Trire 2.0 69494 does not have a methionine residue at its N-terminus suggesting that the annotation is not completely accurate. For the purpose of the present Examples, it was assumed that the correct N-terminus was located 126-amino acid residues upstream of the first residue in the JGI annotated sequence. The total length of the predicted DCL1 protein in *T. reesei* exceeds 1,400 amino acid residues providing ample target for gene disruption. Protein ID 69494 in Trire 2.0 shows the highest homology to the *N. crassa* DCL2 protein and is herein referred to as the *T. reesei* DCL2 protein, with the gene encoding it being referred to as dcl2.

B. Making a dcl1 Disruption Vector

The DNA constructs used for the disruption followed the same approach as the constructs previously used for disruption of cellulase genes (see, e.g., WO2012/054554 and US2012107872). The disruption cassettes included the following segments (sequentially from 5' to 3'): (i) a 5'-flanking region of 1-1.5 kb pyr2 marker gene, (ii) a "repeat" region of 0.5-0.7 kb selected from the original chromosomal sequence further upstream from the 5'-flanking region and, finally, (iii) a 3'-flanking region of 1-1.5 kb. This approach is illustrated by FIG. 1.

The assembly of such a disruption cassette many be carried in very many different ways using standard techniques. Alternatively, a disruption cassette may be synthesized de novo. The particular method used to disrupt the dcl1 gene is described in detail, below. The primers are listed in Table 1.

TABLE 1

PCR primers used for construction of dcl1 disruption vector

| Primer | Primer sequence | SEQ ID NO |
|---|---|---|
| DCL1_3 | 5'-CTTACCCAACGCGAACGATTGC TAGCTCTGGGCTAC-3' | 1 |
| DCL1_31 | 5'-CTGTGCTAGGTGACGGCTCTCCTTGGT GCCAGTATGCGAAGCTTTCTTTG-3' | 2 |
| DCL1_51 | 5'-CATACTGGCACCAAGGAGAGCCGTCA CCTAGCACAGGGCCATACGGACGGC-3' | 3 |
| DCL1_5 | 5'-GCGCCCAGGAAGCAGCGGCAACAGCAGC AGCAGGAG-3' | 4 |
| DCL1R_5 | 5'-GGTGTCGACTCTAGATCTTCAGCCCATTAT TGCTCCAGGCGGACTGGCCAAG-3' | 5 |
| DCL1R_3 | 5'-CTGTGGGATCCAGATTTGGAAGACTTGAT ACGGGTTC-3' | 6 |
| oPYR2_35 | 5'-TTGCAATTGACTAGTGGATCCAACGCCGGC TATTAGGCCATAAG-3' | 7 |
| oPYR2_55 | 5'-AGTACTAGTCAATTGCTCGAGTTTATAAGT GACAACATGC-3' | 8 |

TABLE 2

PCR primers used for construction of dcl2 disruption vector

| Primer | Primer sequence | SEQ ID NO |
|---|---|---|
| oDCL2_36 | 5'-GTTGGATAGGTACCTAGATGTAAGATTCTA TATAAGTC-3' | 9 |
| DCL2_56 | 5'-CATCTTCATCATCGGCAGCCCACGTAACC TGTGCCAG-3' | 10 |
| DCL2_57 | 5'-CAGGCGAAAGAGGAGGAGATCTCAAAATT CGTCCCCGAAGGCTCGTGGACCAGTG-3' | 11 |
| DCL2_37 | 5'-TTCGGGGACGAATTTTGAGATCTCCTCCT CTTTCGCCTGCCACTTCAAGATCGCAG-3' | 12 |
| DCL2_56 | 5'-CATCTTCATCATCGGCAGCCCACGTAACCT GTGCCAG-3' | 13 |
| DCL2_57 | 5'-CAGGCGAAAGAGGAGGAGATCTCAAAATT CGTCCCCGAAGGCTCGTGGACCAGTG-3' | 14 |
| oDCL2R_3 | 5'-GGTTGGATCCGCGGAAAGGTCAATAAAATG GGAGTTACTGAG-3' | 15 |
| oDCL2R_5 | 5'-GGTTGTCGACTCTAGATCTGCCCTGTCCAG CATCGAGCTGACCTCTCTATTG-3' | 16 |

First, the areas designated the 5'-flanking region and the 3'-flanking region (FIG. 2) were amplified using primer pairs DCL_5 plus DCL_31 and DCL_51 plus DCL_3, respectively, using chromosomal DNA of *T. reesei* 653MU was used as the template. The 1.6 and 1.5 kb products were purified by agarose gel electrophoresis, mixed at about 1:1 ratio and used as a template for a PCR reaction with a pair of primers DCL_5 plus DCL_3 to produce a fusion product of 3.1 kb. The fragment was cloned into the pCR™-Blunt II-TOPO® vector using a kit provided by Invitrogen, thereby generating plasmid pCR(DCL1UD).

In parallel, the dcl1 repeat region (FIG. 2) was amplified with the primers DCL1R_5 plus DCL1R_3 and the pyr2 gene of *T. reesei* was amplified with primers oPYR2_55 and oPYR2_35, both using chromosomal DNA of *T. reesei* 653MU as the template. Both fragments were separately cloned into the pCR™-Blunt II-TOPO® vector resulting in plasmids pCR(DCL1R) and pCR(FlexiPyr2), respectively. Plasmid pCR(DCL1UD) was digested with restriction endonucleases SalI and BglII and the DNA fragment of 5.7 kb was isolated by preparative agarose electrophoresis. Plasmid pCR(DCL1R) was digested with XbaI and BamHI excising a fragment of 0.6 kb containing the dcl1 repeat region. Plasmid pCR(FlexiPyr2) was digested with XhoI and SpeI excising a fragment of 1.7 kb containing the pyr2 gene. Following purification, these two DNA fragments were incubated with the SalI plus BglII-digested pCR(DCL1UD) vector in the presence of DNA ligase, relying on the compatible ends produced by XhoI and SalI, SpeI and XbaI, and BamHI and BglII. The resulting vector pCR(DCL1RPyr) carried the final assembly of the dcl1 gene disruption cassette.

C. Making a dcl2 Disruption Vector

The construction of dcl2 disruption vectors was carried out in similar way to that of dcl1. The method is described in detail, below and the primers are listed in Table 1.

The 5'-flanking (1.6 kb) and 3'-flanking (1.3 kb) regions were amplified by PCR using primer pairs oDCL2_56 plus oDCL2_37 and oDCL2_57 plus oDCL2_36, respectively. Fusion PCR was carried out by purifying the two PCR products by agarose gel electrophoresis and using their mixture as a template for a reaction with primers oDCL2_56 plus oDCL2_36. The resulting 2.9 kb fusion product was cloned into the pCR™-Blunt II-TOPO® vector to generate plasmid pCR(DCL2_UD).

The dcl1 repeat region (0.7 kb) was amplified with oDCL2R_5 plus oDCLR_3. The PCR product was digested with XbaI and BamHI. pCR(DCL2_UD) was digested with SalI and BglII and the large fragment purified. The pyr2 gene was excised from pCR(FlexiPyr2) by digestion with XbaI and SpeI as before. The three fragments were incubated together in the presence of DNA ligase to produce the dcl2 gene disruption vector, pCR(DCL2RPyr, again relying on the compatible ends produced by SpeI and XbaI, and BamHI and BglII.

To produce a *T. reesei* strain with a disrupt dcl1 gene, strain 653MU was transformed with an about 4.4 kb PCR product obtained using pCR(DCL1RPyr) as template and DCL1_5 plus DCL1_3 as primers. A set of stable prototrophic transformants was isolated, and their chromosomal DNA isolated and analyzed by PCR using primer pair oDCL1R_D1 plus oDCL1D_R1 (Table 3 and FIG. 3). Generation of a PCR product of 1.67 kb indicated that the transforming DNA has been homologously integrated at the dcl1 locus of *T. reesei* chromosome. The DNA of one such clone was additionally analyzed using primers oDCL1R_D1 plus oDCL1D_R2. Appearance of a product of 1.8 kb confirmed the correct integration of the disruption cassette at the dcl1 locus. The transformant carrying the disrupted dcl1 gene was allowed to sporulate and the spore suspension has been plated on minimal agar medium supplemented with 1.2 g/L fluoroorotic acid (FOA). Because of the presence of two copies of the "repeat region" in the chromosome of this strain (FIG. 4A), FOA-resistant pyr2-mutants are generated at high frequency by homologous recombination between the two repeat sequences. During a process often referred to as "looping out," the DNA between the two copies of the repeat sequence is lost generating the structure depicted in FIG. 4B. To verify the correct structure of the dcl1 chromosomal area after deletion of the dcl1 gene and excision of the pyr2 marker, DNA was extracted from several FOA resistant isolates. PCR analyses using primer pairs oDCL1FU_D1 plus oDCL1D_R2 and oDCL1FU_D2 plus oDCL1D_R1 resulted in detection of PCR products of 2.3 and 2.4 kb respectively in all tested clones. This is the size of PCR products expected for the chromosomal structure around the deleted dcl1 gene after marker excision (FIG. 4B). One of these FOA-resistant clones generating the expected PCR products was designated strain 356MUΔdcl1.

TABLE 3

Primers used for mapping dcl1 and dcl2 deletions

| Primer | Sequence | SEQ ID NO |
|---|---|---|
| oDCL1D_R1 | 5'-CAGACTCGGACGTCGACTCCTTTC GTGGCAAGTATC-3' | 17 |
| oDCL1D_R2 | 5'-GGGAGATGATTCTTGCGGCGAATCC ATCTTCATCTC-3' | 18 |
| oDCL1FU_D1 | 5'-CCATGTCATTTCACCAGAGACAGCAA ATGTCGGAAG-3' | 19 |
| oDCL1FU_D2 | 5'-CCATCAAGAAGATTGAGGAGGCCATC AAAGACCTCGG-3' | 20 |
| oDCL1R_D1 | 5'-GAGCGCTTTATGACAAGCAATGACAG AGGGCAACTG-3' | 21 |
| oDCL2_5F | 5'-CTAATTTCAGTATTCTAGGTCATGCTA CGCAATAAC-3' | 22 |
| oDCL2D_R1 | 5'-CCAATCAAACACCACCACCACTCAGA ATCTGCATCCTC-3' | 23 |
| oDCL2D_R2 | 5'-CCAGCCAACCCTCGACTCAAAAGAAGA CCAAAACTCCG-3' | 24 |
| oDCL2R_D1 | 5'-GTGCATTAATTAGTCACTGCTACCAAT GGTGATTCCTG-3' | 25 |
| oDCL2R_D2 | 5'-GAAGGTGATGATGACGGTCTGCCTACA TACCTTAGATC-3' | 26 |

Strain 356MUΔdcl1 was converted to uridine prototrophy by transformation with a 4.75 kb PCR product generated using plasmid pCR(DCL2RPyr) as template and primers oDCL2_56 plus oDCL2_36 as primers. Stable prototrophic transformants were screened by isolating the chromosomal DNA of individual clones and performing PCR analysis using primer pairs oDCL2R_D1 plus oDCL2D_R1. A transformant that generated the PCR product of the expected size (1.86 kb) was further analyzed with a different set of primers (oDCL2R_D2 and oDCL2D_R2). A PCR product of 2.1 kb was observed confirming that in this clone the disruption cassette has integrated at the dcl2 site (FIG. 5B). This clone was subjected to the marker excision procedure using FOA in the same fashion as described above. An FOA resistant clone was analyzed by PCR using primers oDCL2_5F and oDCLD_R1. A PCR product of expected size (2.4 kb) was obtained, cloned in PCR™-Blunt II-TOPO® vector, and subjected to DNA sequencing. Sequencing data confirmed that the dcl2 chromosomal locus had the expected structure after deletion of dcl2 gene and excision of the pyr2 marker. The strain that passed all PCR and sequencing checks was named DiMorph and used to study the effects of inactivation of the quelling system in T. reesei.

Example 2.

Testing the Expression of Proteins of Interest in Quelling-competent and Quelling-disrupted and Strains of T. reesei We used two different secreted proteolytic proteins to examine the effect of inactivating the quelling system in T. reesei. One protein is homologous to aminopeptidase Y in various organisms and is referred to as APY (Protein ID 81070 in Trire 2.0). The other protein is a homolog of aminopeptidyl tripeptidases and is referred to as 3PP (Protein ID 82623 in Trire 2.0). The expression cassettes for APY and 3PP were constructed using functional elements that are used routinely in T. reesei expression work. Expression was driven by a cbhI promoter and the coding sequence is flanked on the 3'-end bya cbhI transcriptional terminator. For each gene of interest, two similar expression vectors were constructed: (i) a vector carrying the amdS marker gene (i.e., pTrex3gM(APY) and pTrex3gM(3PP) and (ii) a vector carrying the pyr2 marker gene (i.e., pTrex8gM(APY) and pTrex8gM(3PP).

The methods for assembling the expression cassettes are routine methods of genetic engineering and are not described here in detail. Briefly, the coding sequences of APY and 3PP genes were amplified by PCR, and cloned into the pENTR™/D TOPO® vector (Invitrogen), followed by insertion of the cloned coding sequences between the cbhI promoter and terminator using the Gateway® LR Clonase® Enzyme MIX (Invitrogen). The APY and 3PP expression cassettes could alternatively be ordered from a commercial DNA synthesis service provider. Expression cassettes without bacterial vector sequences were prepared using the aforementioned vectors as templates and the primers listed in Table 4. Primer oTrex3_AMP_5 was used in all reactions as the sense prime. Primer oTrex3_Amds_3 was used as anti-sense primer to amplify expression cassettes carrying the amdS marker (using pTrex3gM(APY) and pTrex3gM (3PP) as templates) and primer oTrex8_Pyr2_3 was used similarly to amplify cassettes carrying the pyr2 marker (using pTrex8gM(APY) and pTrex8gM(3PP) as templates). Finally, antisense-primer oCBHT_3 was used (using pTrex3gM(APY) and pTrex3gM(3PP) as templates) to amplify markerless expression cassettes used as "passenger" DNA in co-transformation experiments.

TABLE 4

Primers used to amplify expression cassettes for APY and 3PP genes

| Primer | Sequence | SEQ ID NO |
|---|---|---|
| oCBHT_3 | 5'-TGGTACTGGGATACACGAAGAG CGGCGATTCTACGGGTTATG-3' | 27 |
| oTrex3_AmdS_3 | 5'-CTAGACTGGAAACGCAACCCT GAAGGGATTCTTCCTTTG-3' | 28 |
| oTrex3_AMP_5 | 5'-GTATAGTAATACGAGTCGCAT CTAAATACTCCGAAGC-3' | 29 |

TABLE 4-continued

Primers used to amplify expression cassettes for APY and 3PP genes

| Primer | Sequence | SEQ ID NO |
|---|---|---|
| oTrex8_Pyr2_3 | 5'-GGAGGGGACGATACACGCACCA TGGACCCCAGTGGGGAAGC-3' | 30 |

To evaluate the effect of quelling-disruption on the expression of protein of interest, DiMorph and an almost isogenic quelling-positive *T. reesei* strain, CelluLight (653MU carrying an additional deletion of the egl4 gene encoding endoglucanase 4) were transformed with the APY and 3PP expression cassettes using pyr2 as the transformation marker. For each transformation experiment about 10 µg of PCR product carrying pyr2 and 30 µg of markerless expression cassette (carrying the same gene of interest) were used. The transformation was performed using the standard protoplast-PEG method (Penttilä, M. et al. (1987) *Gene* 61:155-164.

Figure 6:
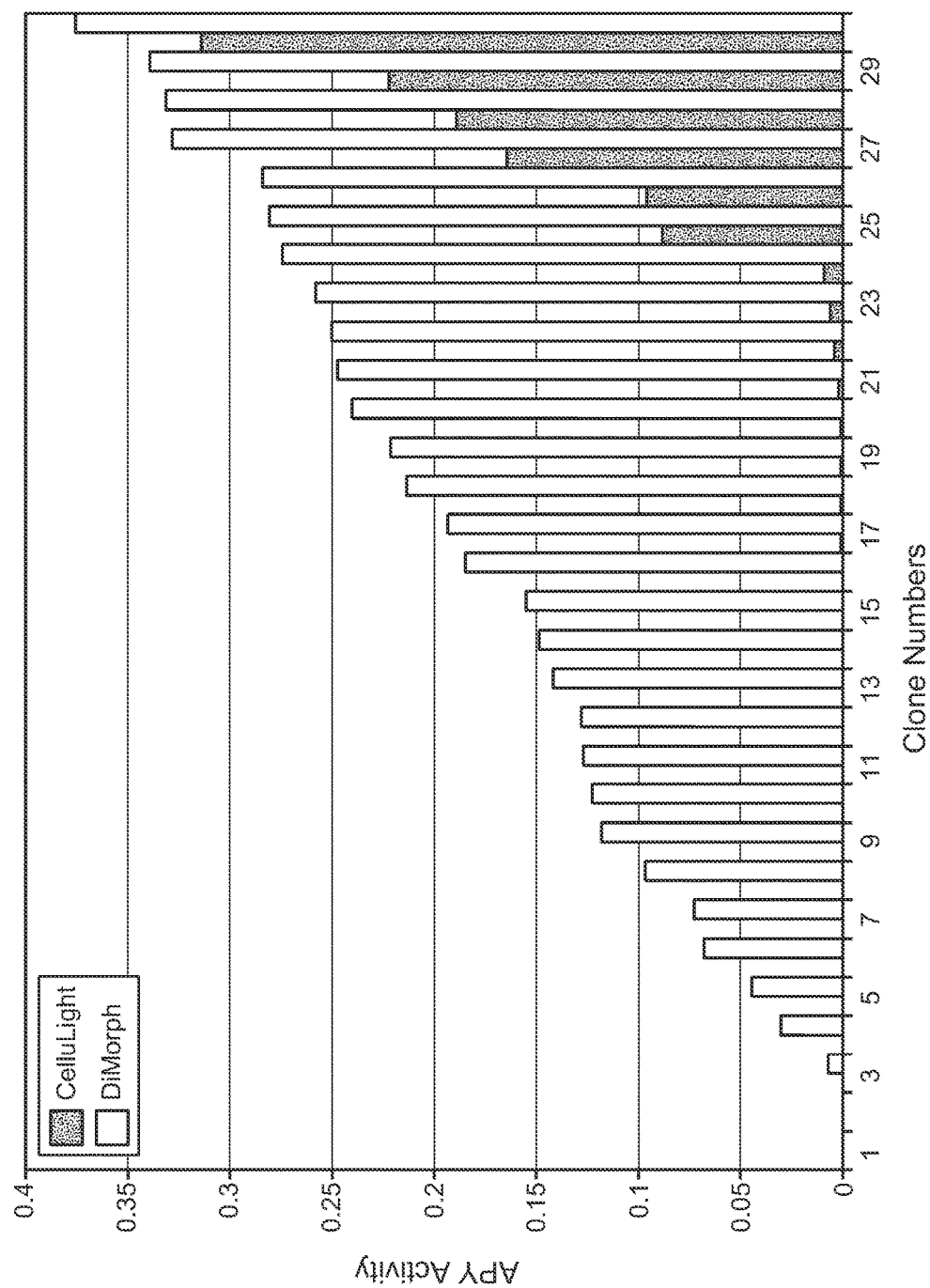
FIG. 6 is a bar graph showing the levels of aminopeptidase Y (APY) activity measured in individual transformants of the two *T. reesei* strains, i.e., DiMorph (manipulated to reduce RNAi) and CelluLight (wild type with respect to RNAi). Both strains were transformed with the same DNA fragment containing the APY expression cassette. Activity was measured in a random set of transformants. Each bar represents APY activity detected in a single clone. The data are sorted from lowest to highest activity (separately for each of the two strains).
Figure 7:
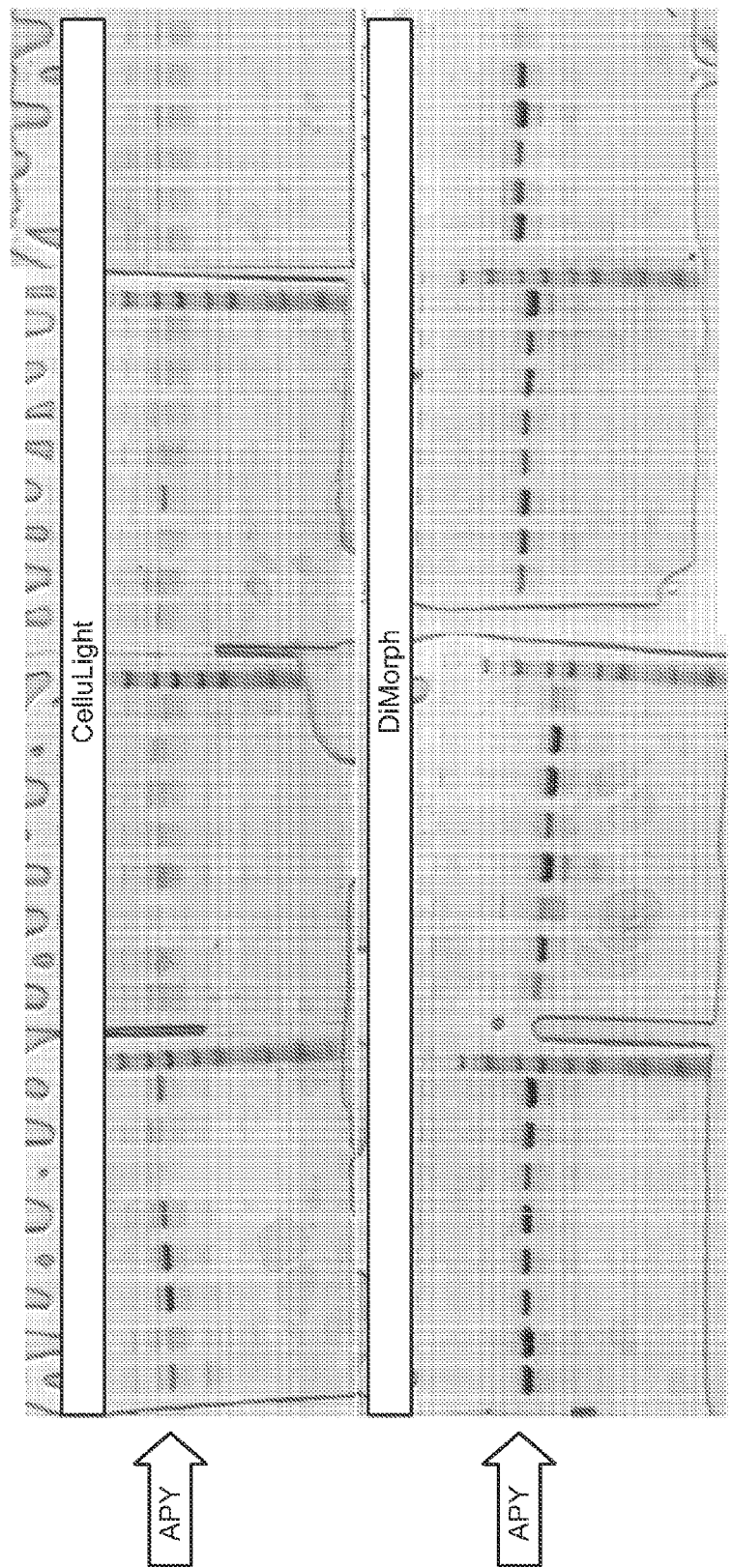
FIG. 7 shows the results of SDS-PAGE analysis of APY expression in DiMorph and CelluLight transformants. Culture supernatants were separated by SDS-PAGE and strained with the SIMPLYBLUE™ reagent (Invitrogen). Each well represents a single transformant (in random order).

In a first experiment using the DiMorph and CelluLight strains transformed with the APY expression cassette using the pyr2 marker, about 30 transformants of each strain that exhibited stable phenotypes were cultivated for 6 days in glycine-sophorose medium (glycine 6 g/L; ammonium sulfate 4.7 g/L; potassium dihydrogen phosphate 5 g/L; magnesium sulfate heptahydrate 1 g/L; PIPPS 33 g/L; and post autoclaving calcium chloride 1 g/L; glucose 16 g/L and sophorose 0.3 g/L). The aminopeptidase activity of the APY protein was assayed in 0.1 M Tris-HCl buffer, pH 7.5 containing 1 mM zinc chloride and 2 mM Lys-p-nitroanilide at room temperature (25° C.). The reaction was followed kinetically at 410 nm. As can be seen from the bar graph in FIG. 6, the distribution of APY activities in the two sets of transformants was very different. About half of all transformants in the quelling-positive CelluLight strain produced no measurable APY activity, while in quelling-disrupted DiMorph strain almost all transformants produced APY. Both average and maximum levels of expression were clearly higher in the quelling-disrupted strain. The observations based on activity measurements closely correlated with the SDS-PAGE data (FIG. 7).

Figure 8:
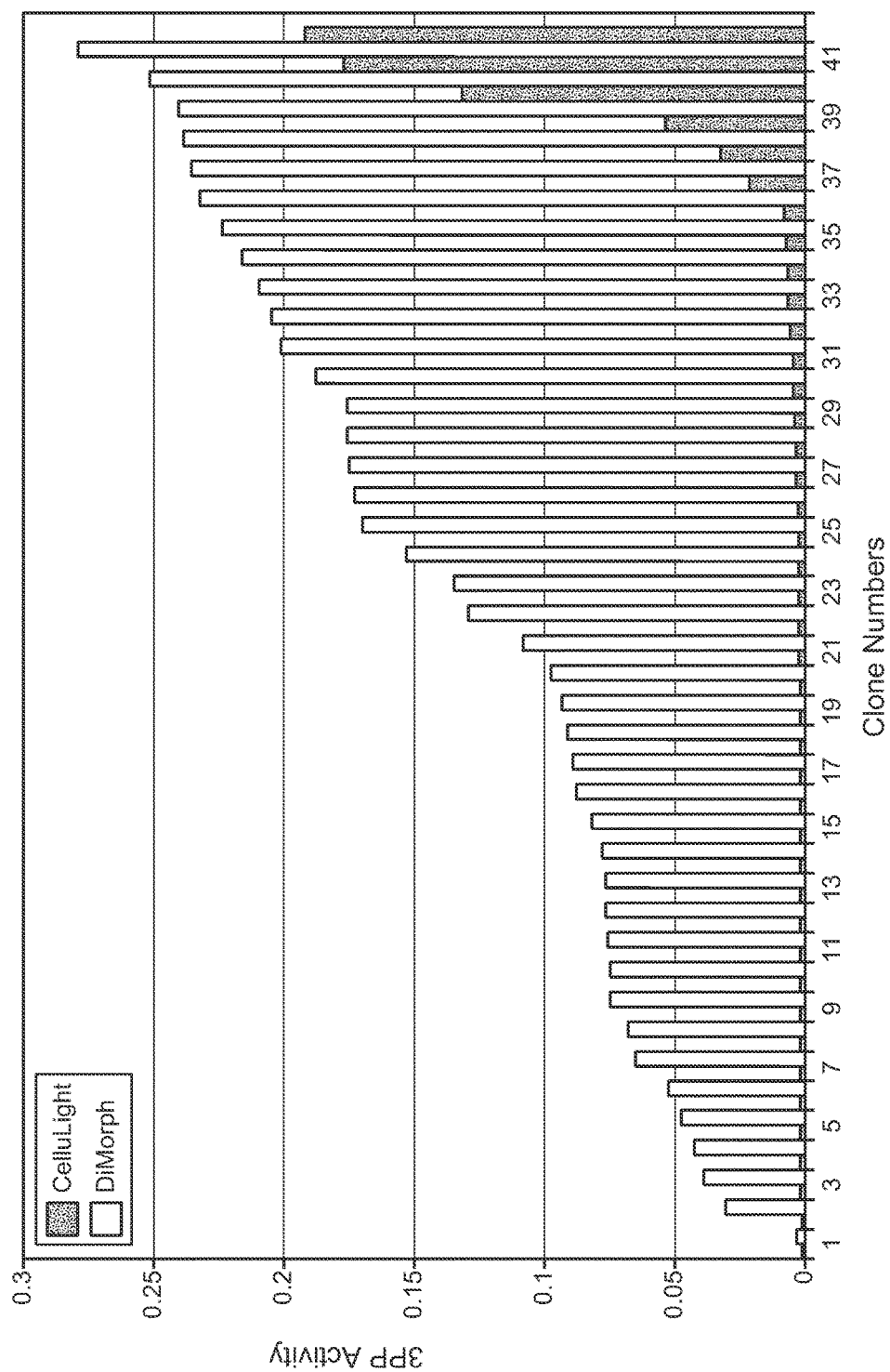
FIG. 8 is a bar graph showing the levels of aminopeptidyl tripeptidase (3PP) activity measured in individual DiMorph and CelluLight transformants containing the 3PP expression cassette. Activity was measured in a random set of transformants. Each bar represents 3PP activity detected in a single clone. The data are sorted from lowest to highest activity (separately for each of the two strains).

In a second experiment using the DiMorph and CelluLight strains transformed with the 3PP expression cassette using the pyr2 marker, about 40 transformants of each strain that exhibited stable phenotypes were cultivated in inducing medium as above. The transformants were then assayed for tripeptidase activity using the tripeptide derivative Ala-Ala-Phe-p-nitroanilide (AAPN; Bachem) as a substrate. The assay was performed in 0.1 sodium acetate buffer, pH 4.0, with 1 mM AAPN at room temperature with the kinetic release of p-nitroaniline measured by absorbance at 410 nm. The results were similar to those obtained in APY expression experiment although the contrast between the expression efficiency in quelling-disrupted and quelling-competent strains (DiMorph and CelluLight, respectively) was even more striking (FIG. 8). Almost all DiMorph transformants produced substantial tripeptidase activity, while only a few CelluLight transformants produced significant tripeptidase activity. Both average and maximum levels of expression were clearly higher in the quelling-disrupted strain.

Example 3.

Figure 9:
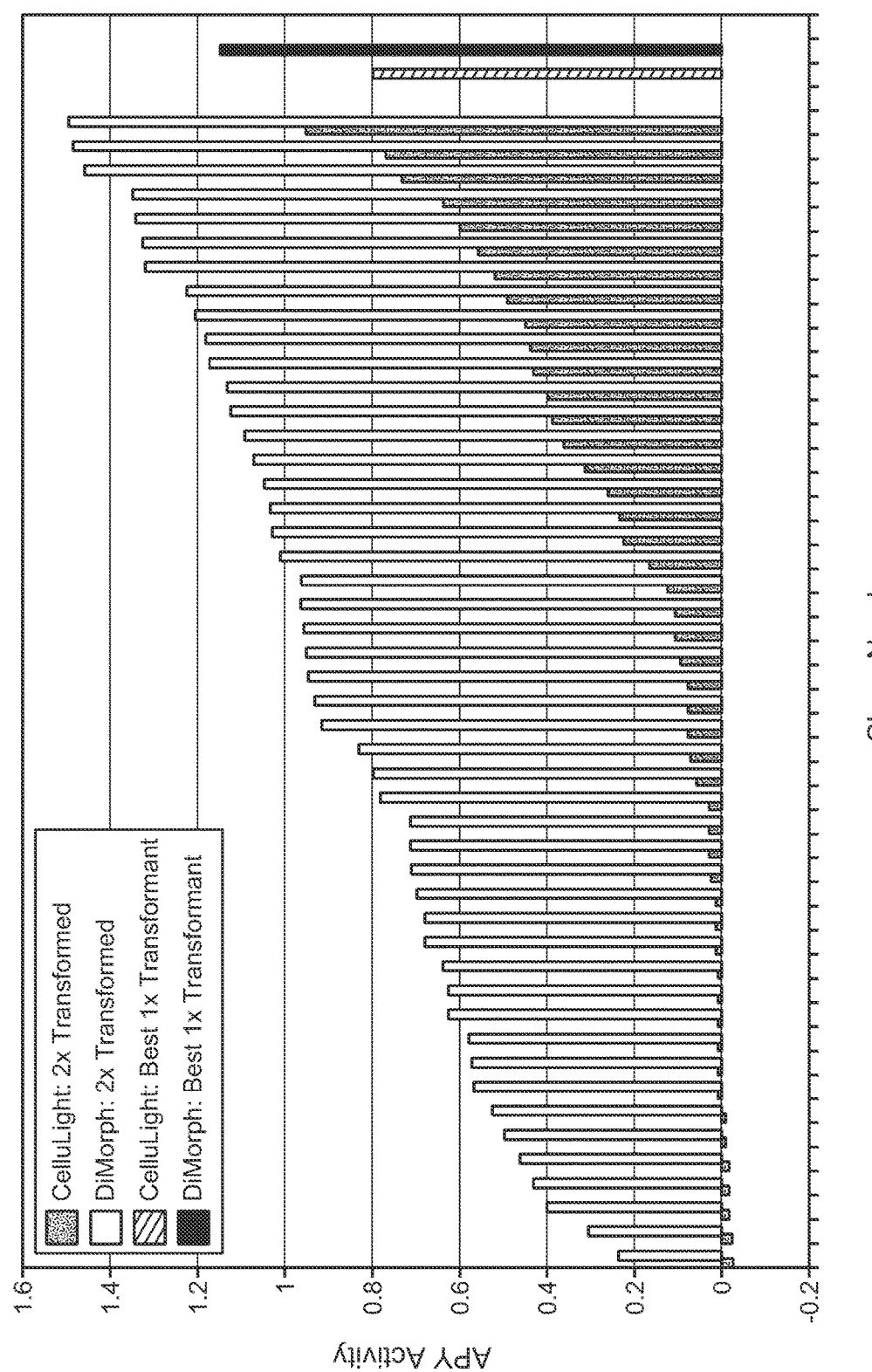
FIG. 9 is a bar graph showing the levels of APY activity measured in individual DiMorph and CelluLight transformants after two rounds of transformation with APY expression cassettes using two different markers. Each bar (except the two bars on the right side of the graph) represents a single second-round transformant. The two bars on the right represent the best single round transformants of CelluLight and DiMorph strains, which were used as transformation hosts for the second round of transformation.

Effect of Repeated Rounds of Transformation on Expression Levels of Proteins of Interest in Quelling-negative and Quelling-positive Strains The highest expressing DiMorph and CelluLight tranformants containing the APY expression cassette with the pyr2 marker from Example 2 were used as hosts for a second round of transformation. The transformation itself was performed in the same way as the first round transformation except that the amdS gene was used as selectable marker. 48 stable, double-transformants derived from either DiMorph or CelluLight hosts were grown in glycine-sophorose medium and assayed for APY activity as before. In the quelling-competent *T. reesei* strain, only one second-round transformant out of 48 had APY activity that was higher than any of the single round transformant (FIG. 9). A large majority of second-round transformants demonstrated a drop rather than increase in activity after an additional round of transformation. About one third of all double transformants lost all measurable APY activity. With the quelling-disrupted DiMorph strain, the results were different. Although some second-round transformants had APY activity lower than the parent strain, none of them lost APY activity completely, and about one quarter of all double-transformants had more APY activity than their parent single-round transformant. The best APY-expressing strain in DiMorph background had about 50% higher expression level of APY than the best strain in quelling-competent CelluLight background.

Figure 10:
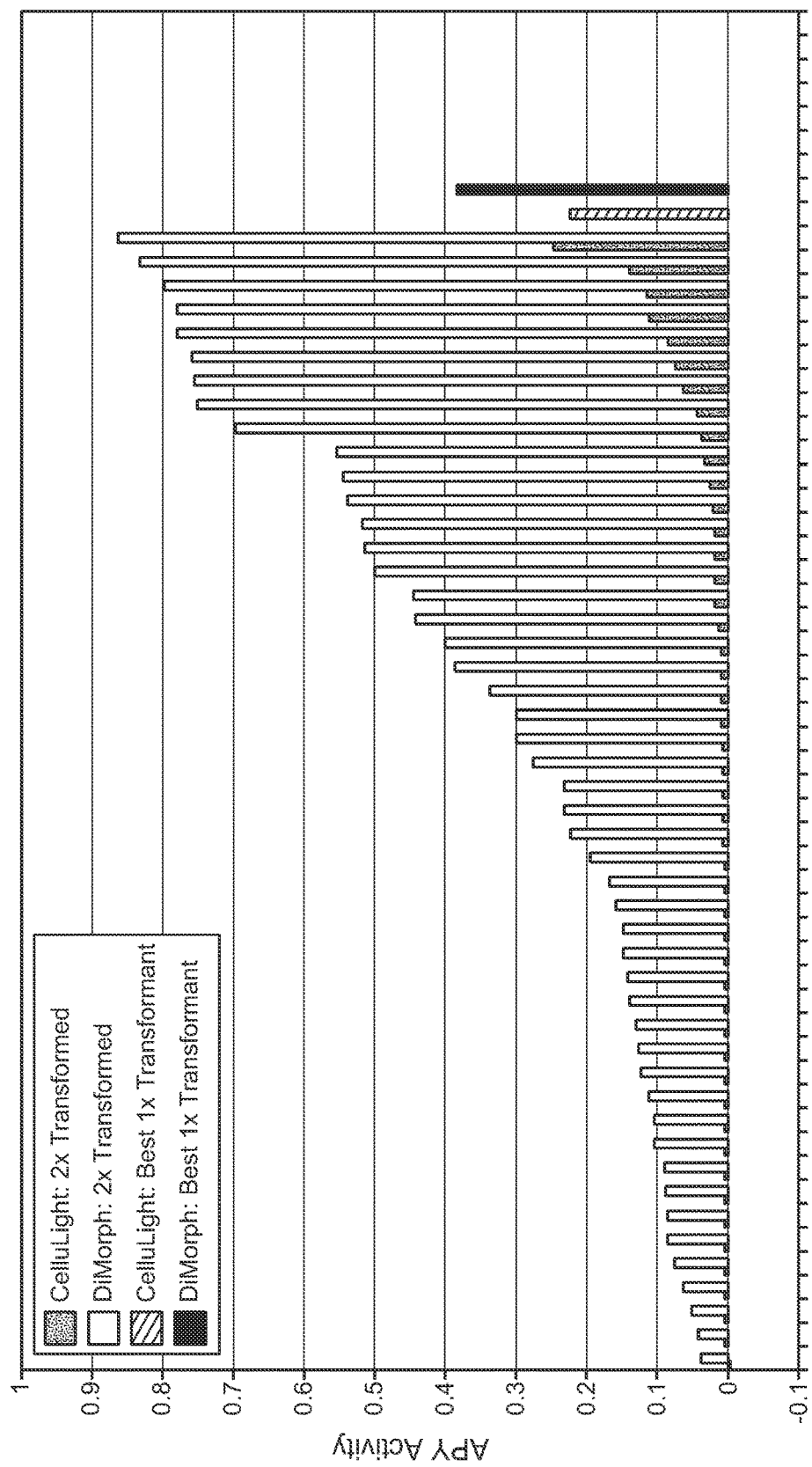
FIG. 10 is a bar graph showing the levels of 3PP activity measured in individual DiMorph and CelluLight transformants after two rounds of transformation with 3PP expression cassettes using two different markers. Each bar (except the two bars on the right side of the graph) represents a single second-round transformant. The two bars on the right represent the best single round transformants of CelluLight and DiMorph strains, which were used as transformation hosts for the second round of transformation.

A similar experiment was performed using the highest expressing DiMorph and CelluLight transformants containing the 3PP expression cassette with the pyr2 marker from Example 2. In this experiment, qualitative trends were similar to those in the experiment on double transformation with APY cassette. However, there were very substantial quantitative differences (FIG. 10). In the quelling-competent strain (CelluLight) most second-round transformants lost most or all 3PP production. Only one double transformant out of 48 showed a marginal improvement over its parent, which was the best the single-round 3PP transformant. In the quelling-disrupted strain (DiMorph), a number of transformants from the second round of transformation have about doubled the expression level relative to their first-round of transformant parent. Again, none of the double transformants in the DiMorph strain completely lost 3PP expression as a result of the additional round of transformation. Remarkably, the best overall DiMorph 3PP transformant (among both single and double-round transformants) was about 3-times more productive than the best CelluLight 3PP transformant.

Example 4.

Testing the Expression of Another Protein of Interest in Quelling-competent and Quelling-disrupted and Strains of *T. reesei*

Additional *T. reesei* strains with disrupted dcl1 and dcl2 genes were made and used to evaluate the expression of other integrated transgenes, including *Aspergillus clavatus* α-amylase and *T. reesei* cellobiohydrolase 2 (CBH2), both under control the *T. reesei* cellobiohydrolase 1 (CBH1) promoter. In both cases, the maximum levels of protein expression, and the average levels of protein expression among a plurality of transformants, was greater in the *T.* reesei cells with disrupted dcl1 and dcl2 genes compared to equivalent cells with an intact RNA interference mechanism (data not shown).

Although the foregoing compositions and methods have been described in some detail by way of illustration and examples for purposes of clarity of understanding, it will be apparent to those skilled in the art that certain changes and modifications may be made. Therefore, the description should not be construed as limiting the scope of the invention, which is delineated by the appended claims.

All publications, patents, and patent applications cited herein are hereby incorporated by reference in their entireties for all purposes and to the same extent as if each individual publication, patent, or patent application were specifically and individually indicated to be so incorporated by reference.

What is claimed is:

1. A method for increasing the expression level of a transgene in *Pezizomycotina* species fungal cells, comprising introducing a genetic alteration into the fungal cells, which genetic alteration reduces the amount of RNA interference in the cells compared to the amount of RNA interference in the absence of the genetic alteration, wherein the genetic alteration comprises a disruption or deletion of a Dicer-like 1 gene (dcl-1) or a dcl-2 gene, wherein the cells produce substantially the same amount of total protein per unit amount of biomass compared to the amount of protein per unit amount of biomass produced by equivalent cells lacking the genetic alteration.

2. The method of claim 1, wherein the genetic alteration is a gene disruption.

3. The method of claim 2, wherein the disruption of the gene is the result of mutagenesis of the gene.

4. The method of claim 2, wherein the disruption of the gene is performed using site-specific recombination.

5. The method of claim 2, wherein the disruption of the gene is performed in combination with introducing a selectable marker at the genetic locus of the gene.

6. The method of claim 2, wherein the disruption of the gene is performed in combination with introducing a transgene encoding a protein of interest.

7. The method of claim 1, wherein the fungus is *Trichoderma reesei*.

8. The method of claim 1, further comprising introducing a transgene for expressing a protein of interest into the cells.

9. The method of claim 8, further comprising introducing an additional copy of the transgene into the cells, wherein the levels of expression of the transgene after introducing the additional copy of the transgene into the cells is no lower than the levels of expression of the transgene before introducing the additional copy of the transgene into the cells.

10. The method of claim 9, wherein the transgene encoding the protein of interest is present in the cells prior to introducing the genetic alteration that reduces or prevents RNA interference.

11. The method of claim 9, wherein the transgene encoding the protein of interest is introduced into the cells after introducing the genetic alteration that reduces or prevents RNA interference.

12. The method of claim 1, wherein the genetic alteration is a gene deletion.

13. A *Pezizomycotina* species fungal cell comprising a genetic alteration which genetic alteration reduces the amount of RNA interference in the cells compared to the amount of RNA interference in the absence of the genetic alteration, wherein the genetic alteration comprises a disruption or deletion of a Dicer-like 1 gene (dcl-1) or a dcl-2 gene, wherein the cells produce substantially the same amount of total protein per unit amount of biomass compared to the amount of protein per unit amount of biomass produced by equivalent cells lacking the genetic alteration.

\* \* \* \* \*